United States Patent
Durden

(10) Patent No.: US 9,353,366 B2
(45) Date of Patent: *May 31, 2016

(54) ASPARAGINASE AND TREATING DISEASES ASSOCIATED WITH ASPARAGINE DEPENDENCE

(71) Applicant: Children's Hospital Los Angeles, Los Angeles, CA (US)

(72) Inventor: Donald L. Durden, La Jolla, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/706,132

(22) Filed: May 7, 2015

(65) Prior Publication Data

US 2015/0307866 A1  Oct. 29, 2015

Related U.S. Application Data

(63) Continuation of application No. 14/348,637, filed as application No. PCT/US2012/059379 on Oct. 9, 2012, now Pat. No. 9,051,561.

(60) Provisional application No. 61/545,238.

(51) Int. Cl.

| | |
|---|---|
| *A61K 38/48* | (2006.01) |
| *A61K 38/46* | (2006.01) |
| *C12N 9/00* | (2006.01) |
| *C12N 9/82* | (2006.01) |
| *A61K 38/50* | (2006.01) |

(52) U.S. Cl.
CPC . *C12N 9/82* (2013.01); *A61K 38/50* (2013.01); *C12Y 305/01001* (2013.01); *C07K 2319/034* (2013.01); *C07K 2319/21* (2013.01); *C07K 2319/23* (2013.01); *C07K 2319/42* (2013.01); *C07K 2319/43* (2013.01)

(58) Field of Classification Search
CPC ........... C12N 9/00; A61K 38/00; A61K 38/50
USPC ........................................ 435/183
See application file for complete search history.

(56) References Cited

U.S. PATENT DOCUMENTS

| 9,051,561 B2 | 6/2015 | Durden |
|---|---|---|
| 2002/0102251 A1 | 8/2002 | Durden |

FOREIGN PATENT DOCUMENTS

| EA | 200600931 A1 | 10/2006 |
|---|---|---|
| WO | 134339 | * 11/2009 |

OTHER PUBLICATIONS

International Search Report for PCT/US2012/059379; mailed Jan. 24, 2013.
Lubkowski et al., UNiProt Database, Accession No. P50286, Oct. 1996.
Extended European Search Report Received in EP 12840089.2, mailed May 20, 2015.

\* cited by examiner

*Primary Examiner* — Maryam Monshipouri
(74) *Attorney, Agent, or Firm* — Suzannah K. Sundby, Esq.; Canady + Lortz LLP

(57) ABSTRACT

Disclosed herein are polypeptides which exhibit asparaginase activity and little to no glutaminase activity. The polypeptides have sequences which correspond to *W. succinogenes* asparaginase, but have an amino acid residue other than proline at amino acid position 121. The polypeptides exhibit higher kinetic rates of asparaginase activity to glutaminase activity as compared to *W. succinogenes* asparaginase and Elspar®, an *E. coli* asparaginase.

17 Claims, 8 Drawing Sheets

(SEQ ID NO:7) FORWARD PCR PRIMER (BamHI SITE UNDERLINED)

5'-TCC<u>GGATCC</u>AGCGCCTCTGTTTTGATGGCT-3'

(SEQ ID NO:8) REVERSE PCR PRIMER (EcoRI SITE UNDERLINED)

5'-TG<u>GGAATTC</u>GGTGGAGAAGATCTTTTGGAT-3'

```
ATG GGC AGC AGC CAT CAT CAT CAT CAT CAT AGC AGC GGC CTG GTG CCG
CGC GGC AGC CAT ATG GCT AGC ATG ACT GGT GGA CAG CAA ATG GGT CGC
GGA TCC AGC GCC TCT GTT TTG ATG GCT AAA CCC CAA GTG ACT ATC CTA
GCC ACA GGA GGC ACC ATC GCT GGT TCG GGG GAA TCT AGC GTC AAG AGT
AGC TAC TCT GCT GGA GCA GTC ACC GTT GAT AAG CTT CTT GCA GCC GTC
CCT GCC ATC AAC GAC GTA GCC ACC ATC AAG GGT GAA CAG ATC TCA AGC
ATT GGC TCC CAA GAG ATG ACG GGT AAG GTG TGG CTT AAA CTA GCC AAG
CGT GTC AAT GAG CTC CTC GCC CAA AAA GAG ACC GAA GCC GTG ATC ATC
ACC CAT GGA ACT GAC ACC ATG GAA GAG ACC GCT TTC TTC CTC AAC CTC
ACG GTG AAA AGC CAA AAA CCT GTC GTC CTT GTA GGC GCC ATG CGT CCA
GGC TCT TCC ATG AGT GCT GAT GGC CCC ATG AAT CTC TAT AAC GCC GTG
AAT GTA GCG ATC AAC AAA GCC TCT ACT AAC AAA GGA GTG GTG ATT GTG
ATG AAC GAT GAG ATT CAC GCC GCC AGA GAA GCG ACC AAG CTC AAC ACC
ACC GCA GTC AAT GCA TTT GCT TCG CCC AAC ACA GGT AAA ATC GGC ACA
GTC TAT TAT GGC AAA GTC GAG TAT TTC ACT CAA TCC GTT CGA CCT CAC
ACC CTT GCA AGT GAG TTT GAT ATT AGC AAA ATC GAA GAA CTC CCC AGA
GTC GAT ATT CTT TAC GCT CAC CCG GAT GAT ACT GAT GTT TTA GTC AAT
GCA GCC CTT CAG GCA GGA GCC AAA GGA ATC ATC CAT GCA GGC ATG GGC
AAT GGG AAC CCT TTC CCT TTG ACT CAA AAT GCT CTT GAA AAA GCA GCC
AAA TCA GGC GTA GTC GTC GCT CGA AGC TCT AGA GTG GGC AGT GGT TCC
ACC ACC CAA GAG GCT GAA GTG GAT GAT AAG AAA CTT GGT TTT GTG GCT
ACA GAG AGT CTC AAC CCT CAA AAA GCC AGA GTG CTT CTT ATG TTA GCC
CTC ACC AAA ACT AGT GAT AGA GAG GCG ATC CAA AAG ATC TTC TCC ACC
TAT TAA TCCAAGAAAGGGAATCTCTTCAC
```

THE POLYCAT SEQUENCE WHICH ENCODES THE POLYHISTIDINE RESIDUES. THE ATG START SITE, AND THE TAA STOP CODON ARE SHOWN IN BOLD LETTERS.

Fig. 6

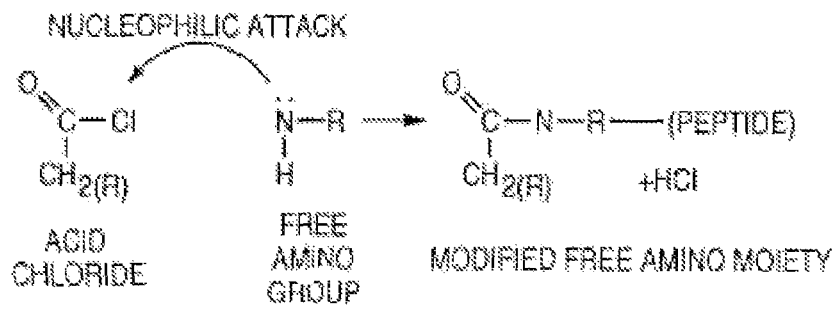

Fig. 7

```
                           SEQUENCE LISTING

<160> NUMBER OF SEQ ID NOS: 10

<210> SEQ ID NO 1
<211> LENGTH: 331
<212> TYPE: PRT
<213> ORGANISM: Artificial Sequence
<220> FEATURE:
<223> OTHER INFORMATION: Derived from W. succinogenes

<400> SEQUENCE: 1

Met Met Ala Lys Pro Gln Val Thr Ile Leu Ala Thr Gly Gly Thr Ile
1               5                   10                  15

Ala Gly Ser Gly Glu Ser Ser Val Lys Ser Ser Tyr Ser Ala Gly Ala
                20                  25                  30

Val Thr Val Asp Lys Leu Leu Ala Ala Val Pro Ala Ile Asn Asp Leu
            35                  40                  45

Ala Thr Ile Lys Gly Glu Gln Ile Ser Ser Ile Gly Ser Gln Glu Met
        50                  55                  60

Thr Gly Lys Val Trp Leu Lys Leu Ala Lys Arg Val Asn Glu Leu Leu
65                  70                  75                  80

Ala Gln Lys Glu Thr Glu Ala Val Ile Ile Thr His Gly Thr Asp Thr
                85                  90                  95

Met Glu Glu Thr Ala Phe Phe Leu Asn Leu Thr Val Lys Ser Gln Lys
            100                 105                 110

Pro Val Val Leu Val Gly Ala Met Arg Ser Gly Ser Ser Met Ser Ala
        115                 120                 125

Asp Gly Pro Met Asn Leu Tyr Asn Ala Val Asn Val Ala Ile Asn Lys
    130                 135                 140

Ala Ser Thr Asn Lys Gly Val Val Ile Val Met Asn Asp Glu Ile His
145                 150                 155                 160

Ala Ala Arg Glu Ala Thr Lys Leu Asn Thr Thr Ala Val Asn Ala Phe
                165                 170                 175

Ala Ser Pro Asn Thr Gly Lys Ile Gly Thr Val Tyr Tyr Gly Lys Val
            180                 185                 190

Glu Tyr Phe Thr Gln Ser Val Arg Pro His Thr Leu Ala Ser Glu Phe
        195                 200                 205

Asp Ile Ser Lys Ile Glu Glu Leu Pro Arg Val Asp Ile Leu Tyr Ala
    210                 215                 220

His Pro Asp Asp Thr Asp Val Leu Val Asn Ala Ala Leu Gln Ala Gly
225                 230                 235                 240

Ala Lys Gly Ile Ile His Ala Gly Met Gly Asn Gly Asn Pro Phe Pro
                245                 250                 255

Leu Thr Gln Asn Ala Leu Glu Lys Ala Ala Lys Ser Gly Val Val Val
            260                 265                 270

Ala Arg Ser Ser Arg Val Gly Ser Gly Ser Thr Thr Gln Glu Ala Glu
        275                 280                 285
```

```
Val Asp Asp Lys Lys Leu Gly Phe Val Ala Thr Glu Ser Leu Asn Pro
    290                 295                 300

Gln Lys Ala Arg Val Leu Leu Met Leu Ala Leu Thr Lys Thr Ser Asp
305                 310                 315                 320

Arg Glu Ala Ile Gln Lys Ile Phe Ser Thr Tyr
                325                 330

<210> SEQ ID NO 2
<211> LENGTH: 330
<212> TYPE: PRT
<213> ORGANISM: Artificial Sequence
<220> FEATURE:
<223> OTHER INFORMATION: Derived from W. succinogenes

<400> SEQUENCE: 2

Met Ala Lys Pro Gln Val Thr Ile Leu Ala Thr Gly Gly Thr Ile Ala
1               5                   10                  15

Gly Ser Gly Glu Ser Ser Val Lys Ser Ser Tyr Ser Ala Gly Ala Val
                20                  25                  30

Thr Val Asp Lys Leu Leu Ala Ala Val Pro Ala Ile Asn Asp Leu Ala
            35                  40                  45

Thr Ile Lys Gly Glu Gln Ile Ser Ser Ile Gly Ser Gln Glu Met Thr
        50                  55                  60

Gly Lys Val Trp Leu Lys Leu Ala Lys Arg Val Asn Glu Leu Leu Ala
65                  70                  75                  80

Gln Lys Glu Thr Glu Ala Val Ile Ile Thr His Gly Thr Asp Thr Met
                85                  90                  95

Glu Glu Thr Ala Phe Phe Leu Asn Leu Thr Val Lys Ser Gln Lys Pro
            100                 105                 110

Val Val Leu Val Gly Ala Met Arg Ser Gly Ser Ser Met Ser Ala Asp
        115                 120                 125

Gly Pro Met Asn Leu Tyr Asn Ala Val Asn Val Ala Ile Asn Lys Ala
130                 135                 140

Ser Thr Asn Lys Gly Val Val Ile Val Met Asn Asp Glu Ile His Ala
145                 150                 155                 160

Ala Arg Glu Ala Thr Lys Leu Asn Thr Thr Ala Val Asn Ala Phe Ala
                165                 170                 175

Ser Pro Asn Thr Gly Lys Ile Gly Thr Val Tyr Tyr Gly Lys Val Glu
            180                 185                 190

Tyr Phe Thr Gln Ser Val Arg Pro His Thr Leu Ala Ser Glu Phe Asp
        195                 200                 205

Ile Ser Lys Ile Glu Glu Leu Pro Arg Val Asp Ile Leu Tyr Ala His
210                 215                 220

Pro Asp Asp Thr Asp Val Leu Val Asn Ala Ala Leu Gln Ala Gly Ala
225                 230                 235                 240

Lys Gly Ile Ile His Ala Gly Met Gly Asn Gly Asn Pro Phe Pro Leu
                245                 250                 255

Thr Gln Asn Ala Leu Glu Lys Ala Ala Lys Ser Gly Val Val Val Ala
            260                 265                 270

Arg Ser Ser Arg Val Gly Ser Gly Ser Thr Thr Gln Glu Ala Glu Val
        275                 280                 285

Asp Asp Lys Lys Leu Gly Phe Val Ala Thr Glu Ser Leu Asn Pro Gln
290                 295                 300

Lys Ala Arg Val Leu Leu Met Leu Ala Leu Thr Lys Thr Ser Asp Arg
305                 310                 315                 320
```

```
Glu Ala Ile Gln Lys Ile Phe Ser Thr Tyr
            325             330

<210> SEQ ID NO 3
<211> LENGTH: 329
<212> TYPE: PRT
<213> ORGANISM: Artificial Sequence
<220> FEATURE:
<223> OTHER INFORMATION: Derived from W. succinogenes

<400> SEQUENCE: 3

Ala Lys Pro Gln Val Thr Ile Leu Ala Thr Gly Gly Thr Ile Ala Gly
1               5                   10                  15

Ser Gly Glu Ser Ser Val Lys Ser Ser Tyr Ser Ala Gly Ala Val Thr
            20                  25                  30

Val Asp Lys Leu Leu Ala Val Pro Ala Ile Asn Asp Leu Ala Thr
        35                  40                  45

Ile Lys Gly Glu Gln Ile Ser Ser Ile Gly Ser Gln Glu Met Thr Gly
    50                  55                  60

Lys Val Trp Leu Lys Leu Ala Lys Arg Val Asn Glu Leu Leu Ala Gln
65                  70                  75                  80

Lys Glu Thr Glu Ala Val Ile Ile Thr His Gly Thr Asp Thr Met Glu
                85                  90                  95

Glu Thr Ala Phe Phe Leu Asn Leu Thr Val Lys Ser Gln Lys Pro Val
            100                 105                 110

Val Leu Val Gly Ala Met Arg Ser Gly Ser Ser Met Ser Ala Asp Gly
        115                 120                 125

Pro Met Asn Leu Tyr Asn Ala Val Asn Val Ala Ile Asn Lys Ala Ser
130                 135                 140

Thr Asn Lys Gly Val Val Ile Val Met Asn Asp Glu Ile His Ala Ala
145                 150                 155                 160

Arg Glu Ala Thr Lys Leu Asn Thr Thr Ala Val Asn Ala Phe Ala Ser
                165                 170                 175

Pro Asn Thr Gly Lys Ile Gly Thr Val Tyr Tyr Gly Lys Val Glu Tyr
            180                 185                 190

Phe Thr Gln Ser Val Arg Pro His Thr Leu Ala Ser Glu Phe Asp Ile
        195                 200                 205

Ser Lys Ile Glu Glu Leu Pro Arg Val Asp Ile Leu Tyr Ala His Pro
210                 215                 220

Asp Asp Thr Asp Val Leu Val Asn Ala Ala Leu Gln Ala Gly Ala Lys
225                 230                 235                 240

Gly Ile Ile His Ala Gly Met Gly Asn Gly Asn Pro Phe Pro Leu Thr
                245                 250                 255

Gln Asn Ala Leu Glu Lys Ala Ala Lys Ser Gly Val Val Val Ala Arg
            260                 265                 270

Ser Ser Arg Val Gly Ser Gly Ser Thr Thr Gln Glu Ala Glu Val Asp
        275                 280                 285

Asp Lys Lys Leu Gly Phe Val Ala Thr Glu Ser Leu Asn Pro Gln Lys
290                 295                 300

Ala Arg Val Leu Leu Met Leu Ala Leu Thr Lys Thr Ser Asp Arg Glu
305                 310                 315                 320

Ala Ile Gln Lys Ile Phe Ser Thr Tyr
            325

<210> SEQ ID NO 4
```

```
<211> LENGTH: 328
<212> TYPE: PRT
<213> ORGANISM: Artificial Sequence
<220> FEATURE:
<223> OTHER INFORMATION: Derived from W. succinogenes

<400> SEQUENCE: 4

Lys Pro Gln Val Thr Ile Leu Ala Thr Gly Thr Ile Ala Gly Ser
1               5                   10                  15

Gly Glu Ser Ser Val Lys Ser Tyr Ser Ala Gly Val Thr Val
            20                  25                  30

Asp Lys Leu Leu Ala Ala Val Pro Ala Ile Asn Asp Leu Ala Thr Ile
            35                  40                  45

Lys Gly Glu Gln Ile Ser Ser Ile Gly Ser Gln Glu Met Thr Gly Lys
    50                  55                  60

Val Trp Leu Lys Leu Ala Lys Arg Val Asn Glu Leu Ala Gln Lys
65                  70                  75                  80

Glu Thr Glu Ala Val Ile Ile Thr His Gly Thr Asp Thr Met Glu Glu
                85                  90                  95

Thr Ala Phe Phe Leu Asn Leu Thr Val Lys Ser Gln Lys Pro Val Val
                100                 105                 110

Leu Val Gly Ala Met Arg Ser Gly Ser Ser Met Ser Ala Asp Gly Pro
                115                 120                 125

Met Asn Leu Tyr Asn Ala Val Asn Val Ala Ile Asn Lys Ala Ser Thr
130                 135                 140

Asn Lys Gly Val Val Ile Val Met Asn Asp Glu Ile His Ala Ala Arg
145                 150                 155                 160

Glu Ala Thr Lys Leu Asn Thr Thr Ala Val Asn Ala Phe Ala Ser Pro
                165                 170                 175

Asn Thr Gly Lys Ile Gly Thr Val Tyr Tyr Gly Lys Val Glu Tyr Phe
                180                 185                 190

Thr Gln Ser Val Arg Pro His Thr Leu Ala Ser Glu Phe Asp Ile Ser
                195                 200                 205

Lys Ile Glu Glu Leu Pro Arg Val Asp Ile Leu Tyr Ala His Pro Asp
210                 215                 220

Asp Thr Asp Val Leu Val Asn Ala Ala Leu Gln Ala Gly Ala Lys Gly
225                 230                 235                 240

Ile Ile His Ala Gly Met Gly Asn Gly Asn Pro Phe Pro Leu Thr Gln
                245                 250                 255

Asn Ala Leu Glu Lys Ala Ala Lys Ser Gly Val Val Ala Arg Ser
                260                 265                 270

Ser Arg Val Gly Ser Gly Ser Thr Thr Gln Glu Ala Glu Val Asp Asp
            275                 280                 285

Lys Lys Leu Gly Phe Val Ala Thr Glu Ser Leu Asn Pro Gln Lys Ala
    290                 295                 300

Arg Val Leu Leu Met Leu Ala Leu Thr Lys Thr Ser Asp Arg Glu Ala
305                 310                 315                 320

Ile Gln Lys Ile Phe Ser Thr Tyr
                325

<210> SEQ ID NO 5
<211> LENGTH: 18
<212> TYPE: PRT
<213> ORGANISM: Artificial Sequence
<220> FEATURE:
<223> OTHER INFORMATION: SRP signal sequence
```

```
<400> SEQUENCE: 5

Lys Lys Ile Trp Leu Ala Leu Ala Gly Leu Val Leu Ala Phe Ser Ala
1               5                   10                  15

Ser Ala

<210> SEQ ID NO 6
<211> LENGTH: 25
<212> TYPE: PRT
<213> ORGANISM: Artificial Sequence
<220> FEATURE:
<223> OTHER INFORMATION: MalE signal sequence

<400> SEQUENCE: 6

Lys Ile Lys Thr Gly Ala Arg Ile Leu Ala Leu Ser Ala Leu Thr Thr
1               5                   10                  15

Met Met Phe Ser Ala Ser Ala Leu Ala
            20                  25

<210> SEQ ID NO 7
<211> LENGTH: 30
<212> TYPE: DNA
<213> ORGANISM: Artificial Sequence
<220> FEATURE:
<223> OTHER INFORMATION: Forward W. succinogenes asparaginase-specific
      PCR primer

<400> SEQUENCE: 7
tccggatcca gcgcctctgt tttgatggct                                    30

<210> SEQ ID NO 8
<211> LENGTH: 30
<212> TYPE: DNA
<213> ORGANISM: Artificial Sequence
<220> FEATURE:
<223> OTHER INFORMATION: Reverse W. succinogenes asparaginase-specific
      PCR primer

<400> SEQUENCE: 8
tgggaattcg gtggagaaga tcttttggat                                    30

<210> SEQ ID NO 9
<211> LENGTH: 1133
<212> TYPE: DNA
<213> ORGANISM: Wolinella succinogenes
<220> FEATURE:
<221> NAME/KEY: CDS
<222> LOCATION: (118)..(1110)

<400> SEQUENCE: 9
atgggcagca gccatcatca tcatcatcat agcagcggcc tggtgccgcg cggcagccat      60
atggctagca tgactggtgg acagcaaatg ggtcgcggat ccagcgcctc tgttttg        117 atg gct aaa ccc caa gtg act atc cta gcc aca gga ggc acc atc gct       165
Met Ala Lys Pro Gln Val Thr Ile Leu Ala Thr Gly Gly Thr Ile Ala
1               5                   10                  15 ggt tcg ggg gaa tct agc gtc aag agt agc tac tct gct gga gca gtc       213
Gly Ser Gly Glu Ser Ser Val Lys Ser Ser Tyr Ser Ala Gly Ala Val
            20                  25                  30 acc gtt gat aag ctt ctt gca gcc gtc cct gcc atc aac gac cta gcc       261
Thr Val Asp Lys Leu Leu Ala Ala Val Pro Ala Ile Asn Asp Leu Ala
        35                  40                  45 acc atc aag ggt gaa cag atc tca agc att ggc tcc caa gag atg acg       309
Thr Ile Lys Gly Glu Gln Ile Ser Ser Ile Gly Ser Gln Glu Met Thr
    50                  55                  60
```

```
ggt aag gtg tgg ctt aaa cta gcc aag cgt gtc aat gag ctc ctc gcc      357
Gly Lys Val Trp Leu Lys Leu Ala Lys Arg Val Asn Glu Leu Leu Ala
 65              70                  75                  80 caa aaa gag acc gaa gcc gtg atc atc acc cat gga act gac acc atg      405
Gln Lys Glu Thr Glu Ala Val Ile Ile Thr His Gly Thr Asp Thr Met
             85                  90                  95 gaa gag acc gct ttc ttc ctc aac ctc acg gtg aaa agc caa aaa cct      453
Glu Glu Thr Ala Phe Phe Leu Asn Leu Thr Val Lys Ser Gln Lys Pro
        100                 105                 110 gtc gtc ctt gta ggc gcc atg cgt cca ggc tct tcc atg agt gct gat      501
Val Val Leu Val Gly Ala Met Arg Pro Gly Ser Ser Met Ser Ala Asp
    115                 120                 125 ggc ccc atg aat ctc tat aac gcc gtg aat gta gcg atc aac aaa gcc      549
Gly Pro Met Asn Leu Tyr Asn Ala Val Asn Val Ala Ile Asn Lys Ala
130                 135                 140 tct act aac aaa gga gtg gtg att gtg atg aac gat gag att cac gcc      597
Ser Thr Asn Lys Gly Val Val Ile Val Met Asn Asp Glu Ile His Ala
145                 150                 155                 160 gcc aga gaa gcg acc aag ctc aac acc acc gca gtc aat gca ttt gct      645
Ala Arg Glu Ala Thr Lys Leu Asn Thr Thr Ala Val Asn Ala Phe Ala
                165                 170                 175 tcg ccc aac aca ggt aaa atc ggc aca gtc tat tat ggc aaa gtc gag      693
Ser Pro Asn Thr Gly Lys Ile Gly Thr Val Tyr Tyr Gly Lys Val Glu
            180                 185                 190 tat ttc act caa tcc gtt cga cct cac acc ctt gca agt gag ttt gat      741
Tyr Phe Thr Gln Ser Val Arg Pro His Thr Leu Ala Ser Glu Phe Asp
        195                 200                 205 att agc aaa atc gaa gaa ctc ccc aga gtc gat att ctt tac gct cac      789
Ile Ser Lys Ile Glu Glu Leu Pro Arg Val Asp Ile Leu Tyr Ala His
    210                 215                 220 ccc gat gat act gat gtt tta gtc aat gca gcc ctt cag gca gga gcc      837
Pro Asp Asp Thr Asp Val Leu Val Asn Ala Ala Leu Gln Ala Gly Ala
225                 230                 235                 240 aaa gga atc atc cat gca ggc atg ggc aat ggg aac cct ttc cct ttg      885
Lys Gly Ile Ile His Ala Gly Met Gly Asn Gly Asn Pro Phe Pro Leu
                245                 250                 255 act caa aat gct ctt gaa aaa gca gcc aaa tca ggc gta gtc gtc gct      933
Thr Gln Asn Ala Leu Glu Lys Ala Ala Lys Ser Gly Val Val Val Ala
            260                 265                 270 cga agc tct aga gtg ggc agt ggt tcc acc acc caa gag gct gaa gtg      981
Arg Ser Ser Arg Val Gly Ser Gly Ser Thr Thr Gln Glu Ala Glu Val
        275                 280                 285 gat gat aag aaa ctt ggt ttt gtg gct aca gag agt ctc aac cct caa     1029
Asp Asp Lys Lys Leu Gly Phe Val Ala Thr Glu Ser Leu Asn Pro Gln
    290                 295                 300 aaa gcc aga gtg ctt ctt atg tta gcc ctc acc aaa act agt gat aga     1077
Lys Ala Arg Val Leu Leu Met Leu Ala Leu Thr Lys Thr Ser Asp Arg
305                 310                 315                 320 gag gcg atc caa aag atc ttc tcc acc tat taa tccaagaaag ggatctctt    1130
Glu Ala Ile Gln Lys Ile Phe Ser Thr Tyr
                325                 330 cac                                                                 1133
```

<210> SEQ ID NO 10
<211> LENGTH: 330
<212> TYPE: PRT
<213> ORGANISM: Wolinella succinogenes

<400> SEQUENCE: 10

```
Met Ala Lys Pro Gln Val Thr Ile Leu Ala Thr Gly Gly Thr Ile Ala
1               5                   10                  15
Gly Ser Gly Glu Ser Ser Val Lys Ser Ser Tyr Ser Ala Gly Ala Val
            20              25              30
Thr Val Asp Lys Leu Leu Ala Ala Val Pro Ala Ile Asn Asp Leu Ala
        35              40              45
Thr Ile Lys Gly Glu Gln Ile Ser Ser Ile Gly Ser Gln Glu Met Thr
    50              55              60
Gly Lys Val Trp Leu Lys Leu Ala Lys Arg Val Asn Glu Leu Leu Ala
65              70              75                      80
Gln Lys Glu Thr Glu Ala Val Ile Ile Thr His Gly Thr Asp Thr Met
            85              90              95
Glu Glu Thr Ala Phe Phe Leu Asn Leu Thr Val Lys Ser Gln Lys Pro
            100             105             110
Val Val Leu Val Gly Ala Met Arg Pro Gly Ser Ser Met Ser Ala Asp
            115             120             125
Gly Pro Met Asn Leu Tyr Asn Ala Val Asn Val Ala Ile Asn Lys Ala
        130             135             140
Ser Thr Asn Lys Gly Val Val Ile Val Met Asn Asp Glu Ile His Ala
145             150             155             160
Ala Arg Glu Ala Thr Lys Leu Asn Thr Thr Ala Val Asn Ala Phe Ala
                165             170             175
Ser Pro Asn Thr Gly Lys Ile Gly Thr Val Tyr Tyr Gly Lys Val Glu
            180             185             190
Tyr Phe Thr Gln Ser Val Arg Pro His Thr Leu Ala Ser Glu Phe Asp
        195             200             205
Ile Ser Lys Ile Glu Glu Leu Pro Arg Val Asp Ile Leu Tyr Ala His
    210             215             220
Pro Asp Asp Thr Asp Val Leu Val Asn Ala Ala Leu Gln Ala Gly Ala
225             230             235             240
Lys Gly Ile Ile His Ala Gly Met Gly Asn Gly Asn Pro Phe Pro Leu
            245             250             255
Thr Gln Asn Ala Leu Glu Lys Ala Ala Lys Ser Gly Val Val Val Ala
            260             265             270
Arg Ser Ser Arg Val Gly Ser Gly Ser Thr Thr Gln Glu Ala Glu Val
        275             280             285
Asp Asp Lys Lys Leu Gly Phe Val Ala Thr Glu Ser Leu Asn Pro Gln
        290             295             300
Lys Ala Arg Val Leu Leu Met Leu Ala Leu Thr Lys Thr Ser Asp Arg
305             310             315             320
Glu Ala Ile Gln Lys Ile Phe Ser Thr Tyr
                325             330
```

ASPARAGINASE AND TREATING DISEASES ASSOCIATED WITH ASPARAGINE DEPENDENCE

CROSS-REFERENCE TO RELATED APPLICATIONS

This application claims the benefit of U.S. Patent Application Ser. No. 61/545,238, filed 10 Oct. 2011, which is herein incorporated by reference in its entirety.

REFERENCE TO A SEQUENCE LISTING SUBMITTED VIA EFS-WEB

The content of the ASCII text file of the sequence listing named "20121009_043833_019_seq_ST25" which is 20.6 kb in size was created on 7 Oct. 2012 and electronically submitted via EFS-Web herewith the application is incorporated herein by reference in its entirety.

BACKGROUND OF THE INVENTION

1. Field of the Invention

The present invention relates to recombinant asparaginase (rWS) which exhibit little to no glutaminase activity and methods and compositions thereof.

2. Description of the Related Art

Asparaginases are enzymes which catalyze the deamidation of L-asparagine (asparaginase activity) and L-glutamine (glutaminase activity). See Cantor, P. S. & Schimmell, M. R., Enzyme Catalysis, 2nd ed., (T. Pettersonn & Y. Tacashi, eds.) Sanders Scientific Press, New York pp. 219-23, (1990) L-glutamine serves as the amide donor in purine biosynthesis, as well as other transamination reactions, and hence plays a role in DNA and cyclic nucleotide metabolism.

In vivo biochemical activity of asparaginase was first documented to be present in guinea pig serum in 1922 (see Clementi, A., La desamidation enzmatique de l'asparagine chez les differentes especes-animals et la signification physiologique de sa presence dass l'organisme, 19 Arch. Intern. Physiol. 369 (1922)). The subsequent discovery that asparaginase isolated from guinea pig serum was the active agent which inhibited the in vivo growth of certain asparagine-dependent mammalian tumors without concomitant deleterious effects on normal tissue (see Broome, J. D., Evidence that the asparaginase activity of guinea pig serum is responsible for its anti-lymphoma effects, 191 Nature 1114 (1961)) suggested that this enzyme could be utilized as an anti-neoplastic agent. Because L-asparagine is a non-essential amino acid, asparaginase was initially thought to represent a unique prototype of selective chemotherapy in which treatment could be directed specifically and selectively against asparagine-dependent cells. However, the low levels of asparaginase in guinea pig serum necessitated the development of a more practical source of this anti-neoplastic enzyme.

Subsequently, microbial asparaginase isolated from *Escherichia coli* and *Erwinia carotovora* were shown to act as potent anti-leukemic agents (see Howard, J. B. & Carpenter, F. H., L-asparaginase from *Erwinia carotovora*: substrate specificity and enzymatic properties, 247 J. Biol. Chem. 1020 (1972); Campbell, H. A., et al., Two asparaginases from *Escherichia coli* B: their separation, purification, and anti-tumor activity, 6 Biochemistry 721 (1967)), and when one of these enzymes was utilized in combination with the chemotherapeutic agent vincristine and the corticosteroid prednisone for the treatment of acute lymphoblastic or acute undifferentiated human leukemia, an overall remission rate of 93% was reported (see Ortega, J. A., et al., L-asparaginase, vincristine, and prednisone for the induction of first remission in acute lymphocytic leukemia, 37 Cancer Res. 535 (1977)).

While these asparaginases possess potent anti-leukemic activity, clinical utilization of the aforementioned microbial asparaginases resulted in a wide range of host toxicity (e.g. hepatic, renal, splenic, pancreatic dysfunction and blood coagulation) and pronounced immunosuppression (see Ohno, R. & Hersh, E. M., Immunosuppressive effects of L-asparaginase, 30 Cancer Res. 1605 (1970)), unlike asparaginase isolated from guinea pig serum (see Cooney, D. A., et al., L-asparaginase and L-asparagine metabolism, 10 Ann. Rev. Pharmacol. 421 (1970)).

Examination of the effects of *E. coli* asparaginase treatment on spleen histology and lymphocyte populations revealed a marked reduction in both the size and reactivity of the splenic germinal centers which was concomitantly associated with a marked reduction in the cytoplasmic immunoglobulin-containing cells (B-cell immunoblasts; see Distasio, J. A., et al., Alteration in spleen lymphoid populations associated with specific amino acid depletion during L-asparaginase treatment, 42 Cancer Res. 252 (1982)). Additionally, examination of the lymphocyte sub-population within the spleen revealed that there was a 40% reduction in the percentage of surface immunoglobulin-expressing cells (B-cells) accompanied by an increase in the ratio of Thy-1.2-expressing cells (T-cells), whereas the ratio of Lyt-2 to Lyt-1 cells remained unchanged in comparison to the control animal group. These results supported the hypothesis that glutamine, or glutamine combined with asparagine depletion initially resulting from administration of *E. coli* asparaginase, caused a marked decrease in spleen lymphocytic cells of the B-cell lineage.

Another important adverse clinical effect associated with traditional microbial asparaginase treatment is hepatic dysfunction (see Schein, P. S., et al., The toxicity of *E. coli* asparaginase, 29 Cancer Res. 426 (1969)). Patients treated with *E. coli* asparaginase generally exhibit decreased plasma levels of albumin, antithrombin III, cholesterol, phospholipids, and triglycerides. Other indications of asparaginase-induced hepatic dysfunction and pathology include fatty degenerative changes, delayed bromosulfophthalein clearance, and increased levels of serum glutamic-oxaloacetic transaminase and alkaline phosphatase. Although some investigators have reported that low dosages of *E. coli* asparaginase result in limited hepatotoxic complications, sensitive indicators of hepatic function in some patients receiving low dosages, however, still reveals significant hepatic disease which may result in life-threatening coagulopathy (see Crowther, D., Asparaginase and human malignant disease, 229 Nature 168 (1971)).

The hepatotoxic effects of microbial asparaginases may be a result of their capability to hydrolyze both asparagine and glutamine. One biochemical difference between *E. coli* and *E. carotovora* asparaginases and the enzyme derived from guinea pig is the non-specific amidohydrolase activity associated with the microbial enzymes (see Howard, J. B. & Carpenter, F. H., (1972) supra; Campbell, H. A., et al., (1967) supra). For example, *E. coli* asparaginase has been shown to possess a 130-fold greater level of glutaminase activity as compared to the activity of *Wolinella succinogenes* (previously classified as *Vibrio succinogenes*) asparaginase. As a result, patients treated with the conventional microbial asparaginases show a marked reduction in serum levels of both glutamine and asparagine (see Schrek, R., et al., Effect of L-glutaminase on transformation and DNA synthesis of normal lymphocytes, 48 Acta Haematol. 12 (1972)), which may demonstrate a possible correlation between glutamine deprivation and asparaginase-induced clinical toxicity (see Spiers, A. D. S., et al., L-glutaminase/L-asparaginase: human pharmacology, toxicology, and activity in acute leukemia, 63 Cancer Treat. Rep. 1019 (1979)).

The relative importance of L-glutamine in mammalian intermediary metabolism served to stimulate further research into the possible role of glutamine deprivation in asparaginase-induced immunosuppression. Lymphoid tissue has been shown to have relatively low levels of glutamine synthetase activity (see El-Asmar, F. A. & Greenberg, D. H., Studies on the mechanism of inhibition of tumor growth by glutaminase, 26 Cancer Res. 116 (1966); Hersh, E. M., L-glutaminase: suppression of lymphocyte blastogenic responses in vitro, 172 Science 139 (1971)), suggesting that these tissues may be particularly sensitive to the depletion of exogenous glutamine. In contrast, some investigators have proposed that asparagine depletion alone may be responsible for asparagine-induced immunosuppression (see Baechtel, F. S., et al., The influence of glutamine, its decomposition products, and glutaminase on the transformation of human lymphocytes, 421 Biochem. Biophys. Acta 33 (1976)).

While the immunosuppressive effect of *E. coli* and *E. carotovora* asparaginases are well-documented (see Crowther, D., (1971) supra; Schwartz, R. S., Immunosuppression by L-asparaginase, 224 Nature 276 (1969)), the molecular biological basis of these functions have not yet been fully elucidated. The inhibition of lymphocyte blastogenesis by various L-glutamine antagonists (see Hersh, E. M. & Brown, B. W., Inhibition of immune response by glutamine antagonism: effect of azotomycin on lymphocyte blastogenesis, 31 Cancer Res. 834 (1980)) and glutaminase from *Escherichia coli* (see Hersh, E. M., (1971) supra) tends to be illustrative of a possible role for glutamine depletion in immunosuppression. It has been also demonstrated that inhibition of the lymphoid blastogenic response to phytohemagglutinin (PHA) by *E. coli* asparaginase can be reversed by the addition of L-glutamine but not by the addition of L-asparagine. See Simberkoff, M. S. & Thomas, L., Reversal by L-glutamine of the inhibition of lymphocyte mitosis caused by *E. coli* asparaginase, 133 Proc. Soc. Exp. Biol. (N.Y.) 642 (1970). Additionally, a correlation between immunosuppression and the relative amount of glutaminase activity has been suggested by the observation that E. asparaginase is more effective than *E. coli* asparaginase in suppressing the response of rabbit leukocytes to PHA (see Ashworth, L. A. E. & MacLennan, A. P., Comparison of L-asparaginases from *Escherichia coli* and *Erwinia carotovora* as immunosuppressant, 34 Cancer Res. 1353 (1974)). However, the significance of these in vitro studies is somewhat limited because the in vivo fates of asparaginases and the homeostatic control of asparagine and glutamine may result in a modification of the immunosuppressive effects of anti-neoplastic asparaginases.

Another significant problem associated with the use of microbial asparaginases is that patients treated with *E. coli* and *E. carotovora* asparaginases frequently develop neutralizing antibodies of the IgG and IgM immunoglobulin class (see, e.g. Cheung, N. & Chau, K., Antibody response to *Escherichia coli* L-asparaginase: Prognostic significance and clinical utility of antibody measurement, 8 Am. J. Pediatric Hematol. Oncol. 99 (1986); Howard, J. B. & Carpenter, F. H. (1972) supra), which allows an immediate rebound of serum levels of asparagine and glutamine. In an attempt to mitigate both the toxic effects and immunosensitivity associated with the therapeutic utilization of *E. coli* and *E. carotovora* asparaginase, a covalently-modified *E. coli* asparaginase (PEG-asparaginase) was initially developed for use in patients who have developed a delayed-type hypersensitivity to preparations "native" of *E. coli* asparaginase (see Gao, S. & Zhao, G., Chemical modification of enzyme molecules to improve their characteristics, 613 Ann. NY Acad. Sci. 460 (1990)). However, subsequent studies established that the initial development of an immune response against *E. coli* asparaginase resulted in an 80% cross-reactivity against the PEG-asparaginase with concomitant adverse pharmacokinetic effects—neutralization of PEG-asparaginase activity and normalization of the plasma levels of L-asparagine and L-glutamine (see Avramis, V. & Periclou, I., Pharmodynamic studies of PEG-asparaginase (PEG-ASNase) in pediatric ALL leukemia patients, Seventh International Congress on Anti-Cancer Treatment, Paris, France (1997)). The development of antibodies directed against *E. coli* (EC) asparaginase and the modified PEG-asparaginase in patients is associated with neutralization of the enzymatic activity of both the EC and PEG-asparaginases in vivo, thus potentially resulting in an adverse clinical prognosis.

Despite a variety of asparaginases known in the art, a need still exists for asparaginases which have little to no glutaminase activity yet exhibit asparaginase activity.

The references cited herein are not admitted to be prior art to the inventions described herein.

SUMMARY OF THE INVENTION

The present invention is directed to asparaginases derived from *W. succinogenes*, particularly 121 analogs thereof. The 121 analogs of the present invention may be obtained using methods known in the art. For example, such methods comprise obtaining nucleic acid coding for a polypeptide comprising unique contiguous amino acid sequence of *W. succinogenes* asparaginase, wherein such amino acid sequence comprises at least nine amino acids, cloning that nucleic acid into an expression vector, introducing the expression vector into an appropriate host cell or population of host cells, culturing the host cell(s) under conditions which allow expression of the polypeptide (here, a 121 analog) in a biologically active form, or a form from which biological activity can be reconstituted.

Proteins (including native and recombinant *W. succinogenes* asparaginase, analogs and derivatives thereof, and acylated asparaginases derived from other sources) produced in accordance with the foregoing methods can be purified and formulated into pharmaceutical compositions. Purification can be accomplished by any suitable process. Such processes typically involve affinity purification processes and/or size separation techniques. After purification, the polypeptide can be formulated into a pharmaceutical composition comprising the enzyme and a pharmaceutically acceptable carrier. Such compositions, and others according to the invention, are the administered to a patient so as to deliver a therapeutically effective amount of the 121 analog. In certain embodiments, such compositions allow for oral delivery, while other embodiments allow for transdermal or transmucosal delivery. Preferred embodiments include those intended for parenteral injection, e.g. via an intramuscular, intravenous or subcutaneous route. Compositions and treatments according to the present invention may comprise one or more additional asparaginases which need not be a 121 analog.

In alternative embodiments, a polypeptide of the present invention is produced in vivo. In certain of these embodiments, the polypeptides so produced will then be isolated from the animal producing them (e.g. a transgenic animal into which the nucleic acid has been introduced). In other embodiments, the polypeptide will be produced by the cells of the patient, as will occur in gene therapy applications of the invention, wherein the nucleic acid molecule encoding *W. succinogenes* asparaginase or an analog thereof is delivered via a viral or non-viral gene delivery vehicle. Preferred viral gene delivery vehicles include recombinant retroviruses, alphaviruses, and adeno-associated viruses. Preferred non-viral systems include liposome- or polycation-associated nucleic acid constructs wherein the *W. succinogenes* asparaginase (or analog thereof) coding region is functionally associated with appropriate regulatory elements, which in some embodiments provide for tissue-specific expression.

A related aspect concerns nucleic acid molecules encoding 121 analogs. Certain embodiments of this aspect are analogs which comprise at least one (in some embodiments, 2, 3, 4, 5, 6, 7, 8, 9, 10, or more) amino acid residue substitutions, deletions, and/or insertions, as compared to the amino acid sequence of the mature, native form of *W. succinogenes* asparaginase (the protein encoded by nucleotide sequence 3 of U.S. Pat. Nos. 6,251,388 and 6,991,788). In some of these embodiments, the nucleic acid, in addition to coding for the respective amino acid alternation(s) which distinguish the protein as a 121 analog, also includes one or more additional nucleotide substitutions which do not result in a change in the amino acid encoded by the codon(s) under consideration. Such conservative substitutions can serve to facilitate cloning (e.g. though introduction of a restriction endonuclease cleavage site) and/or optimize expression, for example, by including one or more codons preferred for expression in the particular host cell (i.e. those codons used in proteins expressed at high levels, as determined by statistical analysis of codons used in proteins which are expressed at high, moderate, or low levels in cells of the host) into which the nucleic acid is to be introduced. Such nucleic acid molecules are typically inserted, or cloned, into an expression vector capable of directing expression of genes functionally inserted therein. In general, such vectors are plasmids which include a promoter (or other transcription activation sequence) at an appropriate distance from the 5'-terminus of the gene(s) to be expressed therefrom. In certain embodiments, the promoter is inducible. The expression vector also preferably encodes one or more selectable markers, which may or may not be separately regulated. In other embodiments, the vector is a component of a gene delivery vehicle. When the gene delivery vehicle is a virus, the vector typically comprises at least the components of the viral genome needed for gene expression and packaging into an infectious particle.

An additional aspect of the invention concerns derivatives of 121 analogs and methods for producing the same. Such derivatives include those which been covalently modified to include a chemical moiety not found in the naturally occurring enzyme. Representative examples of such derivatives include those in which one or more amino acids have been glycosylated (as may occur when a recombinant form of the enzyme is produced in a host cell having the intracellular machinery required for protein glycosylation, e.g. a mammalian host cell), pegylated, acylated, or methylated. Recombinant forms of *W. succinogenes* asparaginase and analogs can be prepared as described above, although when a non-analog form is used for derivativization, the nucleic acid encoding the protein will code for a mature form of the native enzyme.

Yet another aspect of the invention relates to covalent modification of 121 analogs. Certain embodiments of this aspect concern one or more covalent modifications to facilitate isolation/purification of recombinant forms of the enzyme. Other embodiments concern covalent modifications to alter substrate specificity, immuno-reactivity, bio-distribution, serum half-life, etc.

Another aspect of the present is directed to methods for the therapeutic utilization of 121 analogs, alone or in combination with, native and/or recombinant forms of *W. succinogenes* asparaginase and/or variants thereof (which comprise a proline at aa 121) in the treatment of diseases which respond to asparagine depletion and/or asparaginase therapy, including certain neoplasias (e.g. acute lymphoblastic leukemia (ALL) and acute undifferentiated leukemia), as well as in the treatment of various non-malignant hematological and autoimmune diseases which respond to asparagine depletion. These methods involve administering to a patient a therapeutically effective amount of at least one 121 analog. Representative malignant diseases which can be so treated include certain hematologic diseases, for example, lymphomas, leukemias, and myelomas, including both chronic and acute phases. Representative non-malignant diseases which can be treated in accordance with the instant invention include autoimmune diseases, for example, arthritis (e.g. rheumatoid arthritis), SLE, and AIDS. Typically, the instant methods will be applied to humans afflicted with a disease which responds to asparagine depletion and/or asparaginase therapy, although other patient classes, particularly mammals (e.g. bovine, canine, equine, feline, ovine, porcine, and primate animals) suffering from a disease which responds to asparagine depletion and/or asparaginase therapy can be similarly treated.

Still other aspects of the invention concerns host cells containing nucleic acid molecules of the invention. For expression 121 analogs, microbial production systems are preferred, particularly bacterial, yeast, and mammalian cells systems. Another aspect relates to polypeptide derivativization methods using acylation. Preferred embodiments of this aspect relate to acylation of purified asparaginases, particularly *W. succinogenes* asparaginases (derived from both natural and recombinant sources) and analogs thereof. In a related aspect, methods are provided for altering a pharmacokinetic property of protein (e.g. asparaginase, particularly *W. succinogenes* asparaginase or an analog thereof) by acylating the protein.

In some embodiments, a 121 analog of the present invention is an isolated and/or recombinantly produced polypeptide comprising, comprising, consisting essentially of, or consisting of an amino acid sequence that corresponds to the protein encoded by SEQ ID NO:9 (i.e. protein having SEQ ID NO:10) and has an amino acid residue other than proline at amino acid position 121, and optionally a signal sequence linked to its N-terminus. In some embodiments, the 121 analog exhibits a kinetic rate of asparaginase activity that is greater than about 7.5, preferably 7.6 to about 21.8, times that of its kinetic rate of glutaminase activity, or a kinetic rate of asparaginase activity that is between 7.5 to 22 times that of its kinetic rate of glutaminase activity. In some embodiments, the polypeptide has an amino acid sequence that has at least 90-100%, 91-100%, 92-100%, 93-100%, 94-100%, 95-100%, 96-100%, 97-100%, 98-100%, 99-100%, or 100% sequence identity to SEQ ID NO:1, SEQ ID NO:2, SEQ ID NO:3, or SEQ ID NO:4. In some embodiments, the signal sequence is SEQ ID NO:5 or SEQ ID NO:6. In some embodiments, the amino acid residue at aa 121 is serine, alanine, glycine, cysteine, or threonine, preferably serine. In some embodiments, the polypeptide exhibits no glutaminase activity or reduced glutaminase activity as compared to a protein having SEQ ID NO:10.

In some embodiments, the present invention is directed to an isolated nucleic acid molecule which encodes a polypeptide comprising, comprising, consisting essentially of, or consisting of an amino acid sequence that corresponds to the protein encoded by SEQ ID NO:9 (i.e. protein having SEQ ID NO:10) and has an amino acid residue other than proline at amino acid position 121, and optionally a signal sequence linked to its N-terminus. In some embodiments, the 121 analog exhibits a kinetic rate of asparaginase activity that is greater than about 7.5, preferably 7.6 to about 21.8, times that of its kinetic rate of glutaminase activity, or a kinetic rate of asparaginase activity that is between 7.5 to 22 times that of its kinetic rate of glutaminase activity. In some embodiments, the polypeptide has an amino acid sequence that has at least 90-100%, 91-100%, 92-100%, 93-100%, 94-100%, 95-100%, 96-100%, 97-100%, 98-100%, 99-100%, or 100% sequence identity to SEQ ID NO:1, SEQ ID NO:2, SEQ ID NO:3, or SEQ ID NO:4. In some embodiments, the signal sequence is SEQ ID NO:5 or SEQ ID NO:6. In some embodiments, the amino acid residue at aa 121 is serine, alanine, glycine, cysteine, or threonine, preferably serine. In some embodiments, the polypeptide exhibits no glutaminase activity or reduced glutaminase activity as compared to a protein having SEQ ID NO:10. In some embodiments, the present invention is directed to a host cell which contains an isolated nucleic acid molecule as disclosed herein.

In some embodiments, the present invention is directed to a pharmaceutical composition comprising, consisting essentially of, or consisting of, as an active pharmaceutical ingredient, a 121 analog as disclosed herein. In some embodiments, 121 analog is provided in a therapeutically effective amount for treating a disease which responds to asparagine depletion and/or asparaginase therapy.

In some embodiments, the present invention is directed to methods of treating a patient having a disease which responds to asparagine depletion and/or asparaginase therapy which comprises administering to the patient at least one 121 analog or a pharmaceutical composition as disclosed herein.

In some embodiments, the present invention is directed to uses of one or more 121 analogs for the treatment of a disease which responds to asparagine depletion and/or asparaginase therapy.

In some embodiments, the present invention is directed to uses of one or more 121 analogs for the preparation of a medicament for the treatment of a disease which responds to asparagine depletion and/or asparaginase therapy.

In some embodiments, the present invention is directed to kits which comprise at least one 121 analog and/or a pharmaceutical composition as disclosed herein packaged together with a drug delivery device.

Other features and advantages of the invention will be apparent from the following figures, detailed description, examples, and claims.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 6: Illustrates the DNA sequence (SEQ ID NO:9) of the modified *W. succinogenes* asparaginase-specific DNA insert. This sequence contains not only the coding sequence of the native *W. succinogenes* asparaginase (beginning with codon 40 of FIG. 6 and not including the final 23 3'-terminal nucleotides of FIG. 6), but also 39 codons for the N-terminal epitope "tag" shown in FIG. 6.

FIG. 7: Is a schematic representation of a chemical modification for a protein, for example *W. succinogenes* asparaginase.

DETAILED DESCRIPTION OF THE INVENTION

Figures 1, 2:
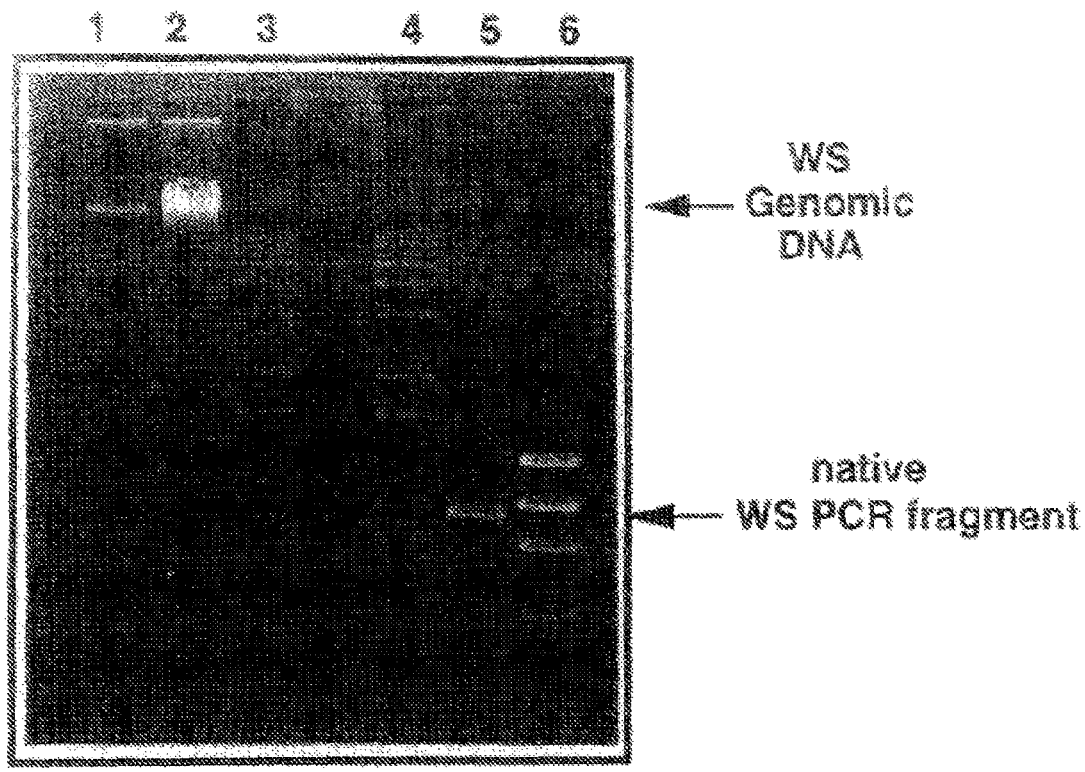
FIG. 1: illustrates the nucleotide sequences of the forward (SEQ ID NO:7) and reverse (SEQ ID NO:8) PCR primers used in the amplification of the genomic L-asparaginase sequences of *W. succinogenes*.
FIG. 2: Agarose gel electrophoresis of propidium iodine-stained *W. succinogenes* genomic DNA (lanes 1 and 2) and a 1.0 kb DNA fragment derived from PCR amplification. Lanes 3 and 4 are DNA molecular weight markers. Lane 5 is the 1.0 kb *W. succinogenes*-specific PCR fragment amplified using the two PCR primers shown in FIG. 1. Lane 6 contains a φX174 DNA molecular weight marker.

As discussed above, the clinical utilization of microbial asparaginases isolated from *E. coli*, *E. carotovora*, and PEG-modified *E. coli* asparaginase in the treatment of leukemia has previously been shown to result in a wide range of host toxicity (e.g. hepatic, renal, splenic, pancreatic dysfunction and blood coagulation), pronounced immunosuppression, and to elicit an allergic-type immunologic reaction with the concomitant formation of neutralizing antibodies, all of which serve to markedly decrease the therapeutic efficacy of these aforementioned microbial asparaginases.

This invention is based on the discovery that particular analogs of *W. succinogenes* asparaginase which have little to no glutaminase activity can be used an alternative form of asparaginase. These particular analogs may be used to treat patients suffering from diseases which respond to asparagine depletion and/or asparaginase therapy, particularly those who have been sensitized to other microbial enzymes by prior treatment. Furthermore, if required, patients initially treated with *W. succinogenes* asparaginase who subsequently develop hypersensitivity to this enzyme will likely be able to receive an immunologically distinct analog of *W. succinogenes* asparaginase or the *E. coli, E. carotovora*, or other covalently-modified asparaginases.

Thus, the present invention relates to polypeptides which exhibit asparaginase activity, but have little to no glutaminase activity, and analogs and fragments thereof. As used herein, the terms "protein", "polypeptide" and "peptide" are used interchangeably. The polypeptides of the present invention may be used as alternative, immunologically distinct asparaginases to treat diseases, such as leukemia, in patients and may allow most patients to complete the full-term course of asparaginase therapy. Moreover, the experimental data provided herein establishes that the polypeptides of the present invention exhibit substantially similar, and perhaps identical, biochemical, pharmacological, and immunological properties as the native, homotetrameric form of the enzyme, with the exception of having little to no glutaminase activity.

The polypeptides of the present invention have amino acid sequences that correspond to those of U.S. Pat. Nos. 6,251,388 and 6,991,788 (which are herein incorporated by reference in their entirety). As used herein, a first sequence that "corresponds" to a second sequence is one that has a sequence that is not 100%, but is at least 95%, at least 96%, at least 97%, at least 98%, or at least 99% identical to the second sequence. A first sequence having a given percent (%) sequence identity with respect to a second sequence is defined as the percentage of amino acid residues (or nucleotide bases) in the first sequence that are identical with the amino acid residues (or nucleotide bases) in the second sequence, after aligning the first and second sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software. Those skilled in the art can determine appropriate parameters for measuring alignment, including any algorithms needed to achieve maximal alignment over the full length of the sequences being compared. For example, the % identity values used herein are generated using WU-BLAST-2 (Altschul et al., *Methods in Enzymology* 266: 460-480 (1996). Most of the WU-BLAST-2 search parameters are set to the default values. For purposes herein, the default parameters of the BLAST alignment tools available online at blast.ncbi.nlm.nih.gov/Blast.cgi may be used.

The polypeptides of the present invention have amino acid sequences that correspond to those of U.S. Pat. Nos. 6,251,388 and 6,991,788, but have an amino acid residue other than proline at amino acid position 121 (aa 121). Thus, the polypeptides of the present invention are sometimes referred to herein as "121 analogs". As used herein, as 121 refers to the amino acid position that corresponds to the position of proline which is encoded by the codon CCA at position 478-480 of the nucleotide sequence 3 of U.S. Pat. Nos. 6,251,388 and 6,991,788 (herein referred to as the "codon 121"). For example, a polypeptide of the present invention may have an amino acid sequence that is less than 121 residues long, e.g. 120 residues long; however, the polypeptide has a sequence that corresponds with a fragment of the protein encoded by sequence 3 (including codon 121). In these embodiments, the amino acid position of the amino acid residue that aligns with the proline encoded by codon 121 of sequence 3 is still referred to as position 121 (aa 121) and the amino acid residue at aa 121 is referred to as "residue 121". Thus, residue 121 of the polypeptides of the present invention is an amino acid other than proline. In some embodiments, residue 121 is serine, alanine, glycine, cysteine, or threonine. In some embodiments, residue 121 is serine. As used herein, "P121" refers to the protein encoded by sequence 3 of U.S. Pat. Nos. 6,251,388 and 6,991,788.

In some embodiments, the polypeptides of the present invention include the following sequences and their corresponding sequences:

```
                                         (SEQ ID NO: 1)
MMAKPQVTILATGGTIAGSGESSVKSSYSAGAVTVDKLLAAVPAI

NDLATIKGEQISSIGSQEMTGKVWLKLAKRVNELLAQKETEAVII

THGTDTMEETAFFLNLTVKSQKPVVLVGAMRSGSSMSADGPMNLY

NAVNVAINKASTNKGVVIVMNDEIHAAREATKLNTTAVNAFASPN

TGKIGTVYYGKVEYFTQSVRPHTLASEFDISKIEELPRVDILYAH

PDDTDVLVNAALQAGAKGIIHAGMGNGNPFPLTQNALEKAAKSGV

VVARSSRVGSGSTTQEAEVDDKKLGFVATESLNPQKARVLLMLAL

TKTSDREAIQKIFSTY (SEQ ID NO: 2)
MAKPQVTILATGGTIAGSGESSVKSSYSAGAVTVDKLLAAVPAIN

DLATIKGEQISSIGSQEMTGKVWLKLAKRVNELLAQKETEAVIIT

HGTDTMEETAFFLNLTVKSQKPVVLVGAMRSGSSMSADGPMNLYN

AVNVAINKASTNKGVVIVMNDEIHAAREATKLNTTAVNAFASPNT

GKIGTVYYGKVEYFTQSVRPHTLASEFDISKIEELPRVDILYAHP

DDTDVLVNAALQAGAKGIIHAGMGNGNPFPLTQNALEKAAKSGVV

VARSSRVGSGSTTQEAEVDDKKLGFVATESLNPQKARVLLMLALT

KTSDREAIQKIFSTY (SEQ ID NO: 3)
AKPQVTILATGGTIAGSGESSVKSSYSAGAVTVDKLLAAVPAIND

LATIKGEQISSIGSQEMTGKVWLKLAKRVNELLAQKETEAVIITH

GTDTMEETAFFLNLTVKSQKPVVLVGAMRSGSSMSADGPMNLYNA

VNVAINKASTNKGVVIVMNDEIHAAREATKLNTTAVNAFASPNTG

KIGTVYYGKVEYFTQSVRPHTLASEFDISKIEELPRVDILYAHPD

DTDVLVNAALQAGAKGIIHAGMGNGNPFPLTQNALEKAAKSGVVV

ARSSRVGSGSTTQEAEVDDKKLGFVATESLNPQKARVLLMLALTK

TSDREAIQKIFSTY (SEQ ID NO: 4)
KPQVTILATGGTIAGSGESSVKSSYSAGAVTVDKLLAAVPAINDL

ATIKGEQISSIGSQEMTGKVWLKLAKRVNELLAQKETEAVIITHG
```

```
TDTMEETAFFLNLTVKSQKPVVLVGAMRSGSSMSADGPMNLYNAV

NVAINKASTNKGVVIVMNDEIHAAREATKLNTTAVNAFASPNTGK

IGTVYYGKVEYFTQSVRPHTLASEFDISKIEELPRVDILYAHPDD

TDVLVNAALQAGAKGIIHAGMGNGNPFPLTQNALEKAAKSGVVVA

RSSRVGSGSTTQEAEVDDKKLGFVATESLNPQKARVLLMLALTKT

SDREAIQKIFSTY
```

The polypeptides of the present invention may further include a signal sequence for periplasmic expression. For example, a signal sequence such as KKIWLALAGLVLAFSASA (SEQ ID NO:5, SRP signal sequence)

KIKTGARILALSALTTMMFSASALA (SEQ ID NO:6, MalE signal sequence)

may be linked to the N-terminus of SEQ ID NO: 1, SEQ ID NO:2, SEQ ID NO:3, or SEQ ID NO:4. Then all or part of the signal sequence cleaved therefrom after expression, e.g. translocation to the periplasm. In some embodiments, the N-terminal methionine residue at the N-terminus of SEQ ID NO:2 is partly cleaved.

In some embodiments, the present invention is directed to nucleic acid molecules (and their complementary sequences) which encode the polypeptides of the present invention. Such nucleic acid molecules include those which encode polypeptides having SEQ ID NO: 1, SEQ ID NO:2, SEQ ID NO:3, and SEQ ID NO:4, with or without a signal sequence such as SEQ ID NO:5 or SEQ ID NO:6. In some embodiments, the nucleic acid molecules are codon optimized for expression by a given host cell, e.g. *E. coli*. As used herein, "nucleic acid molecule" and "polynucleotide" are used interchangeably.

In some embodiments, the polypeptides and/or the nucleic acid molecules of the present invention are isolated and/or purified. An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, a promoter P for expression of protein X is inserted at the 5' end of a nucleic acid molecule which encodes protein Y which nucleic acid molecule does not natively have P at its 5' end. The nucleic acid molecule that encodes protein Y is thus considered to be "isolated". Similarly, a polypeptide that has one or more amino acid residues at its N-terminus and/or C-terminus that are not natively associated with the polypeptide, e.g. an exogenous signal sequence recombinantly added thereto, is considered to be "isolated". As used herein, a "purified" polypeptide or nucleic acid molecule means that some or all of the components, e.g. cellular components, in the composition from which the polypeptide or the nucleic acid molecule was obtained have been removed.

Definition of Terms

Unless otherwise expressly defined, the terms used herein will be understood according to their ordinary meaning in the art, although the following terms will be understood to have the following meanings, unless otherwise indicated.

As provided herein, the polypeptides of the present invention are 121 analogs, i.e. have an amino acid residue that is not proline at as 121. The polypeptides of the present invention may further include analogs of the 121 analogs. An "analog" of a protein, e.g. asparaginase, refers to a polypeptide which differs in some way from the referenced protein. For example, in certain embodiments, an analog of a native asparaginase will refer to a polypeptide in which one or more of its amino acids has been deleted as compared to the corresponding naturally occurring amino acid sequence. Alternatively, one or more amino acid residues may be substituted with a different amino acid. Other analogs include those wherein additional amino acids have been added to the sequence of the referenced protein. For example, one or more amino acids may be added to the amino terminus and/or carboxy-terminus of the polypeptide, or be inserted between internal amino acid residues. Such analogs can be prepared by any suitable technique, although modifying a recombinant gene to encode the desired change(s) will typically be employed. Other analogs include those wherein one or more amino acid residues are derivatized, e.g. glycosylated, pegylated, acylated or otherwise bound covalently to a molecule not attached to the referenced protein. Of course, analogs according to the invention include those wherein an amino acid residue is added to or substituted in the given 121 analog, and the resulting polypeptide itself or one or more of its residues may be later modified, for example, by a covalent modification performed after being at least partially purified or isolated. Moreover, as used herein, an analog includes those that have been modified and exhibit altered biochemical or physiological properties, e.g. different substrate specificity and/or affinity, altered quarternary structure, etc. After generating analogs, e.g. by a rational design strategy, random mutagenesis, etc. the proteins can be screened for biological activity, as described elsewhere herein. When large numbers of analogs are generated, high throughput screen methods are preferred. Those proteins found to exhibit the desired activity in vitro may then be tested in vivo for activity and pharmacokinetic properties. As used herein, "*W. succinogenes* asparaginase" refers to a polypeptide encoded by the nucleotide having sequence 3 as set forth in U.S. Pat. Nos. 6,251,388 and 6,991,788 or variants thereof, but which contain a proline at as 121, i.e. not a 121 analog.

A "unique contiguous amino acid sequence" means an amino acid sequence not found in a naturally occurring protein or polypeptide. For example, a "unique contiguous amino acid sequence of *Wolinella succinogenes*" refers to a sequence which contains one or more amino acid substitutions, insertions, or deletions, as compared to corresponding region of the native sequence.

A "disease which responds to asparagine depletion and/or asparaginase therapy" refers to a disease in which asparagine depletion or treatment with an asparaginase results in an observable improvement in the clinical symptoms of the disease. Depletion or deprivation of asparagine to such cells can be partial or substantially complete, so long as the desired therapeutic benefit is achieved. In certain embodiments, more than about 50% of asparagine in the serum is depleted, preferably greater than about 75%, with depletion of more than 95% being most preferably achieved. Representative examples of diseases which respond to asparagine depletion or deprivation include certain malignant diseases, particularly malignant hematologic diseases, including lymphomas, leukemias and myelomas. Particular examples of leukemias treatable according to the invention include acute lymphyblastic leukemia (ALL), acute non-lymphocytic leukemias, B-cell and T-cell leukemias, chronic leukemias, and acute undifferentiated leukemia. Representative non-malignant hematologic diseases which respond to asparagine depletion include immune system-mediated blood diseases, e.g. infectious diseases such as those caused by HIV infection (i.e.

AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g. ulcerative colitis and Crohn's disease), primary billiary cirrhosis, chronic active hepatitis, glomerulonephritis, myasthenia gravis, pemphigus vulgaris, and Graves' disease. Notwithstanding the foregoing, any disease the cells responsible for which respond, e.g. cease proliferating, become senescent, undergo apoptosis die, etc. to asparagine depletion may be treated in accordance with the instant methods. As those in the art will appreciate, cells suspected of causing a disease which responds to asparagine depletion and/or asparaginase therapy can be tested for asparagine dependence in any suitable in vitro or in vivo assay, e.g. an in vitro assay wherein the growth medium lacks asparagine.

A "patient" refers to an animal afflicted with a disease which responds to asparagine depletion. Typically, patients treated in accordance with the instant methods are mammals, e.g. bovine, canine, equine, feline, ovine, porcine, and primate animals, particularly humans.

An "expression vector" refers to a nucleic acid, typically a plasmid, into which heterologous genes of interest may be cloned and subsequently expressed. For expression, such vectors are generally introduced into a suitable host cell or population of host cells. The expression vector can be introduced by any appropriate technique. Preferred techniques include transformation, electroporation, transfection, and ballistic (e.g. "gene gun") introduction. Depending upon the vector employed, suitable host cells for expression of the desired heterologous gene(s) include prokaryotic and eukaryotic cells. Preferred prokaryotic cells are transformation-competent bacterial cells such as *E. coli* strains DH5α, DH10B, JM 109, BL21, W3110, and the like. Preferred eukaryotic host cells include yeast and mammalian cell lines. As those in the art will appreciate, the particular expression vector/host cell system selected for expression of the desired heterologous gene depends on many factors, and is left to the skilled artisan to determine in the particular circumstances. Similarly, the conditions required for expression of the desired gene from an expression vector carrying the same depends on many factors, including the host cell type, the promoter(s) and other transcription regulation elements employed, the media (or medium) used, etc. Again, the selection made in a given circumstance is at the discretion of the artisan involved, and the particular employed is readily within the skill of such a person given the disclosure herein.

A protein which is "biologically active" is one which has at least one of the biological activities of the corresponding native protein, although the activity exhibited may differ in degree from that of the native protein. For example, an analog according to the invention may have a greater specific activity, longer serum half-life, etc. than the native form of *W. succinogenes* asparaginase.

A protein which comprises an "epitope-tag" refers to one having one or more, preferably two or more, additional amino acids covalently attached thereto, which tag has a distinct epitope which can be recognized by another protein, e.g. an antibody which binds that epitope, preferably with high affinity, a protease which cleaves in or around a specific amino acid sequence (e.g. DAPI, cathepsin-C), etc. For example, as used herein an "N-terminal epitope tag" can refer to a peptide attached to the N-terminus of a protein, wherein the peptide has a conformation recognized by a particular antibody. Such a peptide and its corresponding antibody(ies) can be used to rapidly purify the polypeptide to which the peptide is attached by standard affinity chromatography techniques. Such antibodies, and any others used in the practice of this invention (e.g. for targeting gene delivery vehicles), can be prepared used techniques widely known in the art. For example, see Harlow and Lane in Antibodies, a Laboratory Manual, Cold Spring Harbor Laboratory, 1988. Epitope tags may also be included at the C-terminus of the protein, and in internal regions where insertion of such a tag does not substantially and adversely affect the biological activity or pharmacokinetic properties of the enzyme.

A "therapeutically effective amount" of a protein (e.g. an asparaginase or analog thereof) means that amount required to produce the desired therapeutic effect as compared to a control. Of course, the actual amount required depends on many factors, such as the disease to be treated, the progression of the disease, the age, size, and physical condition of the patient, as discussed in more detail below.

By "altering a pharmacokinetic property of a protein" is meant that a property of a drug as it acts in the body over a period of time, e.g. serum half-life, clearance rate, biodistribution, immunogenecity, etc., is changed. Such alteration can be either an increase or decrease in the property being examined.

Advantages of the Present Invention

As previously discussed, despite its therapeutic utility, microbial asparaginase therapy utilizing *E. coli*, PEG-modified *E. coli*, or *E. carotovora* asparaginases has numerous, distinct clinical limitations, including: (1) hepatic, renal, pancreatic, CNS, and blood coagulation toxicity; (2) the causation of marked immunosuppression; and (3) eliciting an allergic reaction and the production of asparaginase-neutralizing antibodies. In contrast, these limitations are either greatly mitigated or non-existent in therapies with *W. succinogenes* asparaginase, therefore making this enzyme highly efficacious in, for example, the treatment of malignant hematologic diseases and other conditions associated with asparagine dependence, e.g. a disease which responds to asparagine depletion and/or asparaginase therapy.

Described herein are methodologies for the isolation of the "native," homotetrameric *W. succinogenes* asparaginase which possesses potent anti-neoplastic activities, and for the production (using recombinant expression vectors) of rWS and analogs thereof (including 121 analogs), e.g. those which have been acylated or otherwise modified (e.g. by pegylation) and/or modified to include additional or alternate amino acids. In some embodiments, the rWS enzyme is a recombinant form of the native, homotetrameric asparaginase (WS) from *W. succinogenes* (previously *V. succinogenes*; see Durden, D. L., A glutaminase-free asparaginase from *Vibrio succinogenes* lacking immunosuppression and toxicity, Ph. D. Dissertation, University of Miami Medical School (1983); Durden, D. L. & Distasio, J. A., Characterization of the effects of asparaginase from *E. coli* and an asparaginase from *Vibrio succinogenes*, 40 Cancer Res. 1125 (1980)). In some preferred embodiments, the protein is a 121 analog.

The nucleotide sequence encoding the native gene for *W. succinogenes* was determined in 1995, in addition to several hundred bases of 5' and 3' flanking regions (see GenBank accession number X89215). The amino acid sequence and three-dimensional structure of the native enzyme has also been described. See Lubkowski, et al., Eur. J. Biochem., vol. 241:201-207 (1996).

As previously discussed, *W. succinogenes* asparaginase has been shown to be immunologically distinct from the *E.* coli enzyme (see Distasio, J. A. & Niederman, T. (1976), supra). Moreover, previous results have established that *W. succinogenes* asparaginase does not suppress either the humoral or cell-mediated immunological response to the T cell-dependent antigen, SRBC, even when administered in dosages 5-fold higher than the levels of the native *E. coli* enzyme which are capable of completely abrogating these responses (see Durden, D. L. & Distasio, J. A., Characterization of the effects of asparaginases from *Escherichia coli* and a asparaginase from *Vibrio succinogenes* on specific cell-mediated cytotoxicity, 27 Int. J. Cancer 59 (1981); Durden, D. L. & Distasio, J. A. (1980), supra).

The following sections elaborate upon some of the various biochemical and physiological effects of clinical utilization of asparaginase therapy in the treatment of malignant diseases associated with asparagine dependence, particularly hematologic disease, e.g. a disease which responds to asparagine depletion and/or asparaginase therapy.

I. Effects of Asparaginase Treatment on Spleen and Thymus Histology and Lymphocyte Population Examination of the effects of *E. coli* asparaginase treatment on spleen histology and lymphocyte populations are known to cause a marked reduction in both the size and reactivity of the splenic germinal centers, which changes are concomitantly associated with a marked reduction in the cytoplasmic immunoglobulin-containing cells (B-cell immunoblasts; see Distasio, J. A., et al. (1982), supra). Additionally, it is known that spleen lymphocyte sub-populations show up to a 40% reduction in the percentage of surface immunoglobulin-expressing cells (B-cells) accompanied by an increase in the ratio of Thy-1.2-expressing cells (T-cells), whereas the ratio of Lyt-2 to Lyt-1 cells remains unchanged. In contrast, asparagine deprivation alone, caused by the administration of *W. succinogenes* asparaginase, has no demonstrable effect on spleen histology or lymphocyte marker distribution.

Similarly, histological examination of the thymus following *E. coli* asparaginase administration revealed a pronounced depletion of cortical thymocytes, whereas no changes in thymus histology or cellularity were found after *W. succinogenes* asparaginase administration. Therefore, a comparison of the effects of long-term administration on spleen and thymus histology, cellularity, and weight indicated that *E. coli* asparaginase treatment was associated with a pronounced, sustained reduction in these parameters in both the spleen and thymus.

II. Hepatic Toxicity Associated with Asparaginase Administration

Hepatotoxicity is the major clinical toxicity associated with the therapeutic administration of both *E. coli* and *E. carotovora* asparaginases (see Broome, J. D., Factors which may influence the effectiveness of L-asparaginase as tumor inhibitors, 22 Br. J. Cancer 595 (1969)). The hepatotoxic effects of these two microbial enzymes was compared with those associated with the administration of *W. succinogenes* asparaginase (see Durden, D. L., et al., Kinetic analysis of hepatotoxicity associated with anti-neoplastic asparaginases, 43 Cancer Res. 1602 (1983); Distasio, J. A., et al., Glutaminase-free asparaginase from *Vibrio succinogenes*: an anti-lymphoma enzyme lacking hepatotoxicity, 30 Int. J. Cancer 343 (1982)).

Administration of 50 IU of *E. coli* asparaginase to Balb/c mice for 4 days resulted in a diffuse, microfatty infiltration of hepatocytes throughout the liver. In contrast, microscopic examination of cross sections from Balb/c mice treated with *W. succinogenes* asparaginase displayed identical hepatic histology to that of the control animal group. Quantitation of the total amount of extractable lipid from the livers of *E. coli* asparaginase-treated Balb/c mice indicated a 45% and 127% increase in lipid concentration, as compared to the control animal group after 4 and 5 days of treatment, respectively. Administration of *W. succinogenes* asparaginase caused no quantitative change in the total amount of extractable hepatic lipid as compared to the control animal group. In addition, plasma concentration of albumin, triglyceride, and cholesterol, as well as anti-thrombin III activity all were shown to be decreased in Balb/c mice as a result of *E. coli* asparaginase administration, thus confirming hepatotoxicity. The plasma levels of anti-thrombin III were found to be unchanged by administration of *W. succinogenes* asparaginase, and while plasma lipid concentrations were found to be minimally decreased, only the levels of cholesterol were shown to be altered in a statistically way significant from the levels exhibited by the control animals.

In addition, the observed hepatotoxic effects of long-term administration of *E. coli* and *E. carotovora* asparaginases were compared to those of *W. succinogenes* asparaginase. Results obtained from the Balb/c murine model demonstrated that hepatotoxicity associated with the administration of *E. coli* asparaginase paralleled the hepatotoxicity observed in humans, with a rapid increase in total extractable hepatic lipid levels and concomitant decreased plasma levels of albumin, triglyceride, and cholesterol, as well as anti-thrombin III activity occurring in the first and second weeks of treatment, followed by a resumption to normal hepatic function during weeks 3 and 4. Administration of *E. carotovora* asparaginase was associated with an intermediate level of hepatotoxicity, with increased total extractable hepatic lipid concentration occurring during the second and fourth week of treatment. Conversely, prolonged treatment of Balb/c mice with *W. succinogenes* asparaginase was not found to be associated with any demonstrable hepatotoxicity. These results from long-term administration suggest that the observed hepatotoxicity may be a direct result of the combined physiological depletion of asparagine and glutamine.

III. Anti-Neoplastic Activity Associated with Asparaginase Administration

Figure 5:
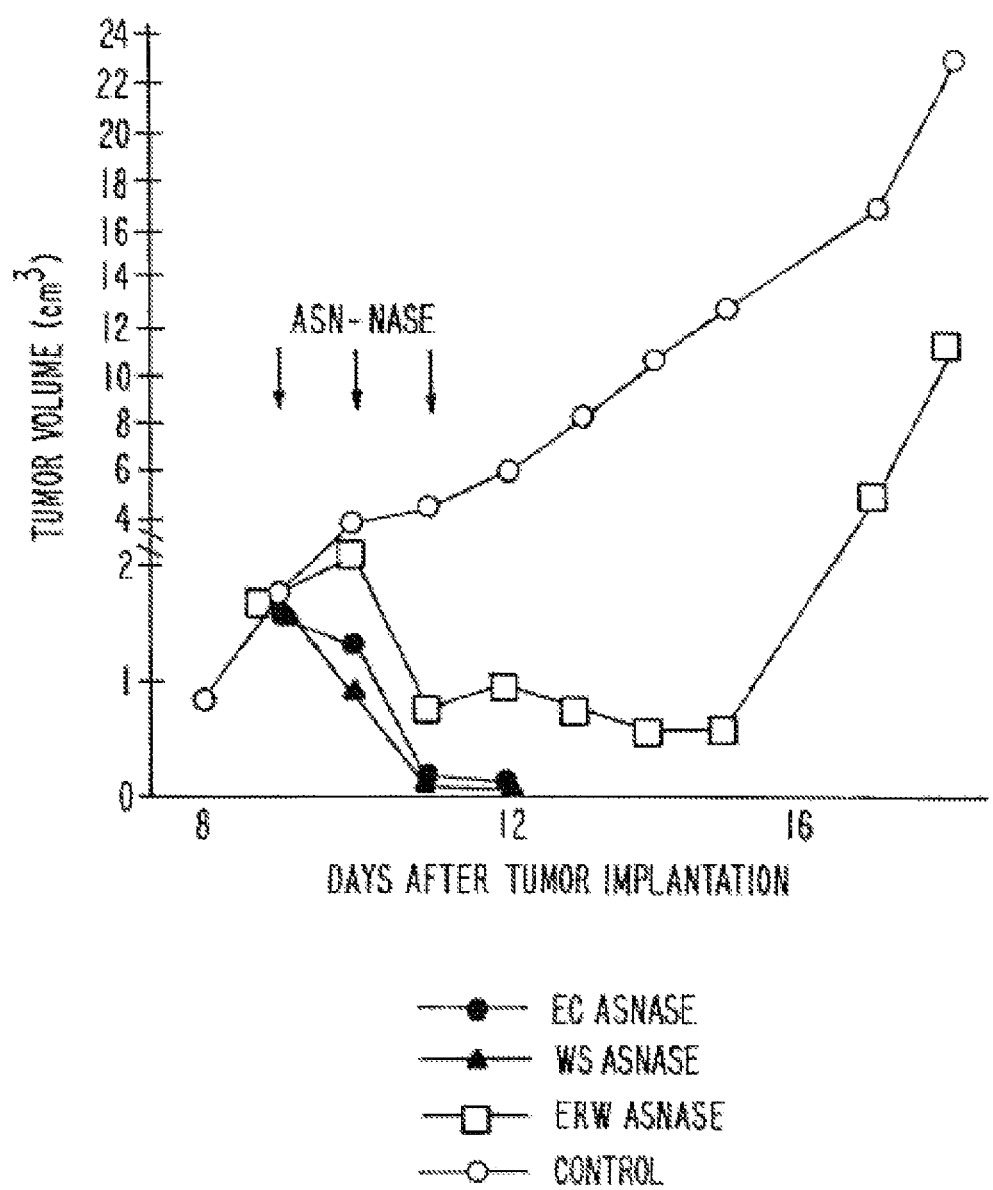
FIG. 5: Illustrates the results of a determination of the anti-tumor activity of *W. succinogenes* (WS), *E. coli* (EC) and *E. carotovora* (Erw) asparaginases against tumors generated by the subcutaneous injection of 6C3HED Gardner lymphosarcoma cells in C3H mice. Anti-tumor activity was measured as a function of caliper-measured tumor volume ($cm^3$). The negative control consisted of injections of 0.01 M phosphate buffer (pH 7.0) into C3H mice using the same injection schedule as for the asparaginases.

The relative anti-neoplastic (anti-lymphoma) activity of native, homotetrameric *E. coli*, *E. carotovora*, and *W. succinogenes* asparaginases were determined against 6C3HED Gardener's lymphosarcoma which had been previously implanted in C3H mice. The results of this study are illustrated in FIG. 5. The control group of animals receiving only 0.01 M phosphate buffer all died within 20 days following initial tumor implantation.

Administration of either *E. coli* or *W. succinogenes* asparaginase resulted in complete remission of the lymphosarcoma in 100% of the animals. The animals were examined for 60 to 90 days following initial tumor implantation with no evidence of tumor. Similarly, animals followed for longer periods of time demonstrated normal longevity with no recurrence of tumor. However, as previously discussed, the utilization of *E. coli* asparaginase is associated with both toxicity and immunosuppression which markedly limits its ability to be used in the treatment of neoplastic disease.

Administration of *E. carotovora* asparaginase resulted in initial regression, followed by a rapid tumor proliferative phase. All animals died (100% mortality) from the development of lymphosarcoma within 30 days post-tumor implantation. Similar results were obtained using the P1798 lymphosarcoma tumor in Balb/c mice.

IV. Immune Cross-Reactivity of Asparaginases

As previously discussed, patients treated with *E. coli* and *E. carotovora* asparaginases frequently develop immunologic delayed-type hypersensitivity reactions with the concomitant production of neutralizing antibodies directed against the specific asparaginase enzyme. Moreover, with the use E. coli asparaginase in the treatment of childhood acute lymphoblastic leukemia (ALL), these aforementioned phenomenon have resulted in a loss of the efficacy of the drug/enzyme and, in some cases, to a recurrence of the leukemia. This immunoreactivity has led to the search for methods to decrease the immunogenicity of asparaginases and to develop other non-cross-reactive forms of this enzyme for clinical use.

Studies have demonstrated that the native, homotetrameric form of *W. succinogenes* asparaginase does not cross-react immunologically with either the *E. coli* (EC) or *E. carotovora* (Erw) asparaginases (see Distasio, J. & Niedennan, A., Purification and characterization of L-asparaginase with anti-lymphoma activity from *Vibrio succinogenes*, 251 J Biol., Chem. 6929 (1976)). Herein, experiments are described herein to evaluate the immunological cross-reactivity of both the native, homotetrameric (WS) and recombinant (rWS) forms of *W. succinogenes* asparaginase using the serum or plasma from patients known to have developed neutralizing antibodies against the EC or Erw asparaginases. In addition, the capacity of the serum or plasma of patients (who have been previously shown to be allergic to EC asparaginase) to cross-react with EC, Erw, WS, and rWS asparaginases has been assessed using a double immunodiffusion assay system. Recent studies suggest that the subclinical detection of anti-EC asparaginase antibodies in patients treated with the EC-derived enzyme is associated with a loss of efficacy of the EC and PEG-asparaginases in vivo (see Avramis, V. & Periclou, I. (1997), supra).

The experimental results described herein demonstrates that it is highly probable that antibodies made in response to xenoimmunization in humans and rabbits to both EC and Erw asparaginase will not cross-react with either WS or rWS asparaginase, nor will they neutralize the enzymatic activity of either form of the enzyme in vivo or in vitro. Similarly, these results also serve to establish that antibodies directed against EC or PEG asparaginase in humans will not cross-react or neutralize WS or rWS asparaginase. Together, these data have provided for developing a rationale for an efficacious clinical application of WS and rWS asparaginase (or analogs thereof) in patients who have previously developed an immunologic-based hypersensitivity to the EC and/or PEG asparaginases.

In addition, due to intrinsic immunosuppressive and anti-metabolic activities, WS and/or rWS asparaginase (or analogs thereof), may also, be utilized in the therapeutic treatment of various autoimmune diseases such as rheumatoid arthritis, systemic lupus erythematosis, AIDS, etc. Although WS asparaginase has less immunosuppressive activity than that of EC asparaginase, the lower level of associated host toxicity makes it ideal for clinical utilization in non-malignant diseases which respond to asparagine depletion.

Covalent Modification of Asparaginases and Other Proteins

Many proteins currently used to treat human diseases have extremely short circulating half-lives which limit their efficacy. In addition, the administration of many foreign proteins (including certain recombinant proteins) is associated with allergic hypersensitivity responses which can also lead to the production of neutralizing antibodies which hasten the rapid elimination of these therapeutic proteins from plasma. To overcome these and other problems, the invention provides a covalent modification procedure to chemically modify proteins, including asparaginases, particularly 121 analogs, in order to extend their half-lives, reduce their immunogenicity, and increase their efficacy. This chemical modification regimen involves the systematic alteration of protein structures by conjugating an aliphatic hydrocarbon chain (be saturated, partially saturated, or unsaturated, a straight chain, a branched chain, and/or a chain of aromatic) of an acylating agent to polar groups within the protein structure (see FIG. 7). While this process is generally applicable to any protein to be introduced into a patient, below conditions are described for covalently modifying *E. coli* and *W. succinogenes* asparaginases using an acid chloride.

Compositions, Formulation, and Administration

As described above, *W. succinogenes* asparaginase (and 121 analogs and derivatives) can be used to treat diseases which respond to asparagine depletion. These compounds may also be used to treat such diseases prophylactically, or to treat those patients previously diagnosed with and treated for such a disease. For example, a patient previously diagnosed and successfully treated for leukemia, or whose disease is otherwise in remission, may experience a relapse. Such patients may also be treated in accordance with the claimed invention.

*W. succinogenes* asparaginase, and its biologically active analogs, e.g. 121 analogs, and derivatives, as well as other acylated asparaginases and proteins, can be administered to a patient using standard techniques. Techniques and formulations generally may be found in Remington's Pharmaceutical Sciences, 18$^{th}$ ed., Mack Publishing Co., Easton, Pa., 1990 (hereby incorporated by reference).

Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the blood stream preferably are soluble.

Pharmaceutical compositions according to the invention can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of an asparaginase may be present as a complex, as those in the art will appreciate.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, supra. Such salts can be prepared using the appropriate corresponding bases.

Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose.

Pharmaceutical compositions according to the invention can be administered by different routes, including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g. intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the asparaginase can be produced.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

The amounts of the active therapeutic agent to be delivered will depend on many factors, including the particular therapeutic agent, for example, a 121 analog, the agent's $IC_{50}$, $EC_{50}$, the biological half-life of the compound, the age, size, weight, and physical condition of the patient, and the disease or disorder to be treated. The importance of these and other factors to be considered are well known to those of ordinary skill in the art. Generally, the amount of asparaginase to be administered will range from about 10 International Units per square meter of the surface area of the patient's body ($IU/M^2$) to 50,000 $IU/M^2$, with a dosage range of about 1,000 $IU/M^2$ to about 15,000 $IU/M^2$ being preferred, and a range of about 6,000 $IU/M^2$ to about 10,000 $IU/M^2$ being particularly preferred to treat a malignant hematologic disease, e.g. leukemia. Typically, these dosages are administered via intramuscular or intravenous injection three times per week, e.g. Monday, Wednesday, and Friday, during the course of therapy. Of course, other dosages and/or treatment regimens may be employed, as determined by the attending physician.

In addition to administering a *W. succinogenes* asparaginase enzyme, such as a 121 analog, to treat a disease which responds to asparagine depletion, other embodiments of the invention concern administration of a nucleic acid construct encoding the enzyme or an analog thereof. As those in the art will appreciate, a variety of different gene delivery vehicles (GDVs) may be employed for this purpose. GDVs include viral and non-viral delivery systems. Representative viral delivery systems include recombinant retroviral vectors which provide for stable, long term, and generally low level expression of one or more heterologous genes via integration in the genome of cells transfected by the virus. Here, retroviral GDVs will encode *W. succinogenes* asparaginase or an analog thereof, and may also include one or more other heterologous genes, for example, a gene encoding a conditionally lethal gene (e.g., thymidine kinase, which converts the pro-drug gancyclovir to its cytotoxic form) to eliminate the transfected cells, if desired.

Other viral delivery systems include those based on adeno-associated virus (AAV) and various alpha viruses, e.g. Sindbis and Venezuelan equine encephalitis virus. These other viral GDVs may provide for higher level expression, or expression for different duration, of the desired heterologous gene(s). As those in the art will appreciate, the host range for the particular virus employed may be altered by techniques well known in the art.

Non-viral GDVs useful in the practice of these embodiments of the invention include, among others, so-called "naked DNA" systems which provide the desired heterologous gene(s) in functional association with an appropriate promoter (which in certain embodiments may be an inducible or tissue-specific promoter) encoded by the nucleic acid construct. Other regulatory elements may also be included, for example, enhancers and other activators of gene expression. Preferably, such non-viral systems are incorporated into liposomes or are associated with polycationic reagents to facilitate introduction of the nucleic acid construct into cells of the patient. Of course, other components can also be included in such GDVs, e.g. molecules to target one or more particular cell types, fusogenic peptides to facilitate endocytotic vesicle escape, etc. Construction of these and other GDVs useful in the practice of this invention are within the skill of those in the art.

EXPERIMENTAL METHODOLOGIES AND RESULTS

The following examples will serve to further illustrate various aspects of the present invention and are not intended to act in any manner as limitations on the claimed invention. In addition, methodologies are provided which will permit one of ordinary skill within the relevant arts to determine whether a 121 analog is appropriate for utilization in the clinical therapeutic treatment of humans. For a discussion of molecular biology techniques which can be used in the practice of this invention, in addition to those described below, see Molecular Cloning, A Laboratory Manual, 4th ed., ed. Sambrook, et al., Cold Spring Harbor Laboratory Press, 2012, and Current Protocols In Molecular Biology, ed. Ausubel, et al., John Wiley & Sons, Inc., 2012.

Example 1

In Vitro Culture of *W. succinogenes*

*W. succinogenes* was grown in 10-15 liters of liquid culture media containing 0.4% yeast extract, 100 mM ammonium formate, and 120 mM sodium fumerate. The medium was adjusted to pH 7.2 prior to autoclaving. After autoclaving, a 0.2 μm filter-sterilized solution of thioglycolate was added to the room temperature culture medium to give a final concentration of 0.05%. The cultures were incubated with continuous agitation on a shaking platform in a 37° C. warm-room. For large scale culture, a 500 ml pre-culture was utilized to inoculate 10-15 liters of complete culture medium.

The bacteria were collected after the cultures had reached an optical density of approximately 1.1 at a 650 nm wavelength, by centrifugation using a Sorvall high-speed continuous flow rotor. Following centrifugation, the cells were washed in a buffer containing 0.15 M sodium chloride, 0.1 M magnesium chloride, and 0.01 M mercaptoethanol. The cells were then resuspended in 0.1 M borate buffer (pH 9.0) at a final concentration of 0.5 g wet cell weight/ml borate buffer and stored frozen until subsequent processing for enzyme purification.

Example 2

Animals and Cell Lines

The murine model animals utilized in these experiments were Balb/C or C3H mice of 9 to 12 weeks in age (Jackson Laboratories, Bar Harbor, Me.).

The therapeutic activity of L-asparaginases was determined utilizing the 6C3HED Gardner's lymphosarcoma (Gardner, W. U., Cancer Res., vol. 4: 73 (1944)) and P1798 lymphosarcoma cell lines (ATCC) which as ascites tumors in C3H and Balb/cc mice, respectively. Alternately, the two lymphosarcoma cell lines were cultured in RPMI 1640 medium supplemented with 10% fetal calf serum. The 6C3HED Gardner's lymphosarcoma originated in the thymus of C3H mice which were initially given high doses of estradiol. The lymphosarcoma was subsequently perpetuated by serial transplantation in the C3H mice.

Example 3

Isolation of *W. succinogenes* Genomic DNA

Genomic DNA from *W. succinogenes* was extracted from bacteria grown in basal medium. Typically, bacterial cells from a 50 ml of culture were collected by centrifugation and resuspended by gentle vortexing in 1.5 ml TE buffer (pH 7.0). To the cell suspension was added 15 µl of 10% SDS to give a final concentration of 0.1% and 3 µl of a 20 mg/ml stock solution of proteinase K. The mixture was then incubated at 37° C. for approximately 60 minutes, followed by several phenol/chloroform extractions. The genomic DNA was ethanol precipitated and collected by centrifugation. The *W. succinogenes* genomic DNA so isolated was sufficiently pure to use in high stringency PCR amplification.

Example 4

PCR Amplification of *W. succinogenes* Asparaginase Sequences

The nucleotide sequence of a 2.5 kb Hind III fragment containing the 993 nucleotide coding region of *W. succinogenes* asparaginase was published in 1995. See GenBank accession number X89215. The elucidation of this sequence facilitated the synthesis of primers specific for PCR amplification of the gene coding, for the *W. succinogenes* enzyme. As illustrated in FIG. 1, the forward and reverse *W. succinogenes* asparaginase-specific PCR primers forward and reverse had the following sequences:

```
Forward PCR Primer
                                         (SEQ ID NO: 7)
5'-TCCGGATCCAGCGCCTCTGTTTTGATGGCT-3'
(BamHI) Restriction Site Underlined)

Reverse PCR Primer
                                         (SEQ ID NO: 8)
5'-TGGGAATTCGGTGGAGAAGATCTTTTGGAT-3'
(EcoR1 Site Restriction Underlined)
```

It should be noted that the genomic *W. succinogenes* asparaginase coding sequence does not naturally contain either a BamH1 or EcoR1 restriction site. However, PCR amplification utilizing these aforementioned primers introduced a BamH1 and EcoR1 restriction site to the 5'- and 3'-termini, respectively to facilitate directional cloning of this amplified genomic sequence into sequencing and/or expression vectors.

With respect to PCR amplification, *W. succinogenes* genomic DNA (purified as per Example 3) was subjected to 30 cycles of PCR amplification under the following reaction conditions: 10 µl PCR II reaction buffer, 6 µl of 25 mg/ml magnesium chloride, 8 µl of 10 mM stock solutions of dNTPs, 1 µl of Taq DNA polymerase (Stratagene Corp.); 1 µl (about 50 ng) each of the *W. succinogenes* asparaginase-specific forward and reverse PCR primers; 1 µl of *W. succinogenes* genomic DNA; and nuclease-free PCR-grade water to bring the reaction mixture to 100 µl total volume. Following amplification, 2 µl of the PCR products were electrophoresed through a 1% agarose gel and stained with propidium iodine to assess both the specificity of the amplification reaction and the molecular weight of the resulting DNA fragments. The amplification resulted in the production of a homogeneous, 1.0 kb *W. succinogenes* asparaginase-specific DNA fragment.

Example 5

Cloning of *W. succinogenes* Asparaginase Sequences

The amplified *W. succinogenes* asparaginase-specific amplified DNA fragment was subsequently sub-cloned into the BamH1 and EcoR1 sites of the PCRII cloning vector (Stratagene, La Jolla, Calif.) utilizing the following reaction conditions: 2 µl of the PCR amplified reaction products, 2 µl of the PCRII cloning vector; 1 µl of 10× ligation buffer; 4 µl of T$_4$ DNA ligase (Stratagene, La Jolla, Calif.); and distilled/deionized water to bring the total reaction volume to 10 µl. The ligation reaction was incubated at 16° C. overnight and 2 µl of this reaction was utilized to transform competent *E. coli* strains DH-5α and M15.

IPTG-induced colorimetric selection (medicated by expression of β-galactosidase in the presence of X-GAL) was utilized to identify recombinant bacterial colonies. Three white colonies (putative positive recombinants) and one blue colony (putative negative recombinants) were chosen, inoculated into a 5 ml culture of LB medium containing 100 µg/ml ampicillin, and incubated overnight at 37° C. on a shaking platform. Plasmid DNA was isolated from these cultures via standard DNA "mini-prep" methodology and the DNA was dissolved in 30 µl TE buffer and digested with 3 different restriction endonucleases: BamH1; EcoR1; and BamH1/EcoR1, to ensure that the isolated plasmid DNA contained the expected 1.0 kb *W. succinogenes* asparaginase-specific insert.

Figure 3:
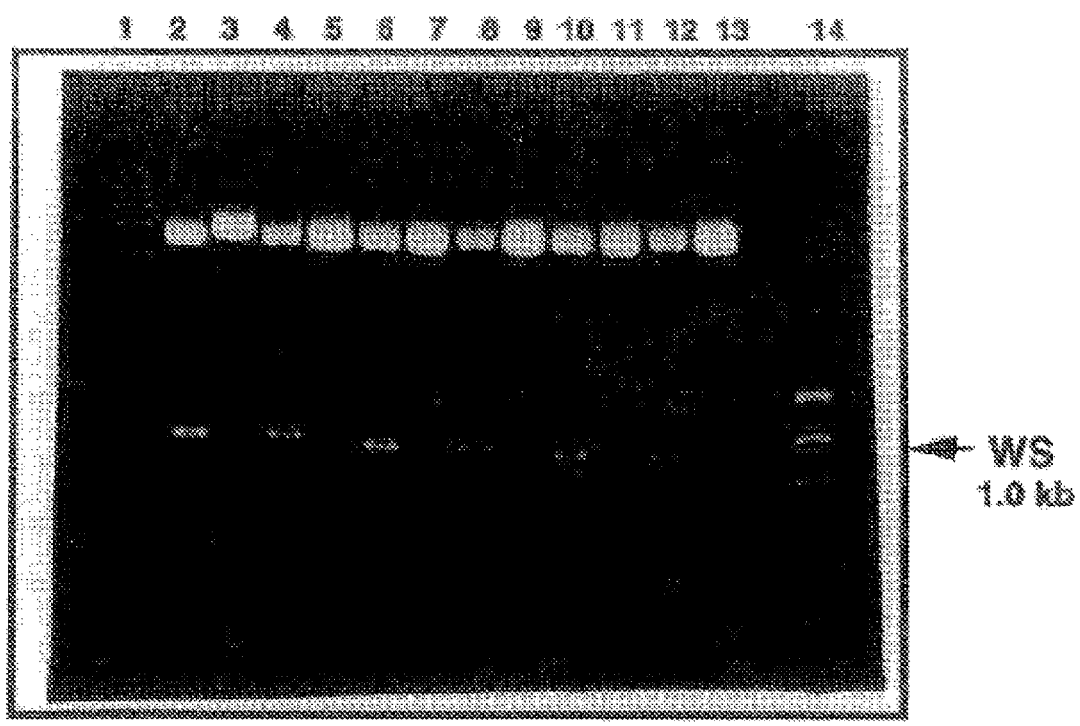
FIG. 3: Restriction enzyme analysis of 4 colonies which were isolated following the ligation of the 1.0 kb *W. succinogenes*-specific PCR fragment into the PCR II vector. The 1.0 kb DNA was digested with BamHI (lanes 2-5); EcoRI (lanes 6-9); and BamH1 and EcoR1 (lanes 10-13). Lane 14 represents a DNA molecular weight ladder. The 1.0 kb *W. succinogenes*-specific DNA fragment is denoted by an arrow.
Figure 4:
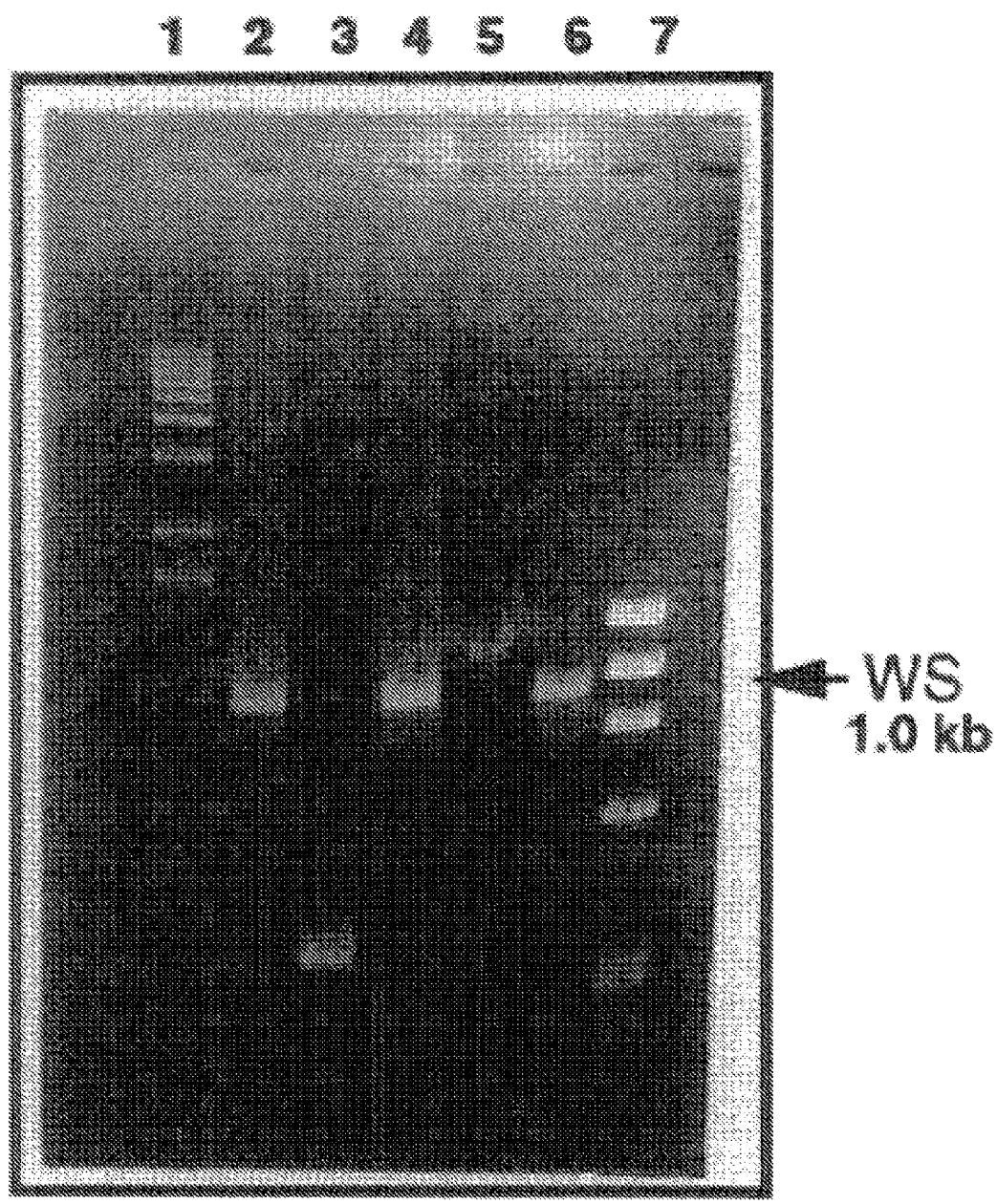
FIG. 4: Agarose gel electrophoresis of the DNA fragments amplified from the selected, "positive" clones utilizing *W. succinogenes* asparaginase-specific primers. Lanes 1 and 7 are molecular weight markers. Lanes 2 and 4 represent DNA extracted from bacterial colonies #1 and #3 from lanes 2 and 4 of FIG. 3. Lane 6 represents a sample of the *W. succinogenes* asparaginase PCR amplification product (amplified from *W. succinogenes* genomic DNA from FIG. 2, lane 5) used in the initial ligation reaction. It should be noted that the fragment cloned into the PCR II vector was shown to be exactly the same size (i.e. 1.0 b) as the initial PCR amplification product.

The electrophoretic results, as illustrated in FIG. 3, lanes 2 and 4, demonstrated that colonies #1 and #3 contained the expected 1.0 kb insert. To confirm that these clones contained the *W. succinogenes* asparaginase gene, the *W. succinogenes* asparaginase-specific PCR primers were used to amplify the *W. succinogenes* asparaginase-specific fragments isolated from the aforementioned clones (FIG. 3, lanes 2 and 4). These primers did not mediate amplification of non-insert-containing bacterial DNA (FIG. 3, lane 3). Results of this second PCR amplification demonstrated that colonies #1 and #3 contained the *W. succinogenes* asparaginase-specific DNA insert within the PCRII cloning vector, resulting in the generation of a 1.0 kb amplification product (see FIG. 3, lanes 2 and 4).

The *W. succinogenes* asparaginase-specific DNA insert in the PCR II cloning vector was then removed by BamH1 and EcoR1 digestion of 10 g of plasmid DNA derived from colony #1, gel-purified via the use of Gene Clean Kit® (Stratagene, La Jolla, Calif.). The DNA insert was eluted from the gel with 10 µl distilled/deionized water and then ligated overnight at 16° C. into the similarly restricted pGEX-2T (Amersham Pharmacia Biotech, Piscataway, N.J.) and pET-28a (Novagen, Inc., Madison, Wis.) vectors under the following reaction conditions: 3 µl DNA insert; 3 µl vector DNA; 4 µl 5× ligation reaction buffer; 1 µl $T_4$ DNA ligase; and 9 µl of distilled/deionized water to give a final reaction volume of 20 µl. 10 µl of each ligation reaction mixture was used to transform 50 µl of competent *E. coli* DH5α cells. Transformants were then plated onto LB agar plates containing 100 mg/ml ampicillin. Positive transformants (i.e. *W. succinogenes* asparaginase-specific DNA insert-containing transformants, pGEX-2T-WSA and pET-28-WSA, respectively) were obtained following approximately 18 hours of incubation at 37° C. To confirm that the transformants contained the *W. succinogenes* asparaginase-specific DNA insert, restriction endonuclease digestion using BamH1 and EcoR1 was performed, as well as PCR amplification and DNA sequence analysis. Results of these analyses demonstrated that each of the selected "positive" transformants contained the *W. succinogenes* asparaginase-specific DNA insert. The nucleotide sequence of the *W. succinogenes* asparaginase-specific DNA insert is shown in FIG. 6 (SEQ ID NO:9), which sequence contains 117 nucleotides 5' to the initial codes of the *Wolinella* gene and 23 nucleotides 3' to the gene's termination codon.

Example 6

Expression of Recombinant *W. succinogenes* Asparaginase Analogs

To facilitate isolation of the recombinant *W. succinogenes* (rWS) asparaginase protein, several types of epitope-labeled asparaginase analogs have been constructed. These epitope labels included: influenza hemagglutinin (HA); glutathione-S-transferase (GST); DYLD (FLAG); and poly-histidine (p-His). In each instance, the label is placed on the N-terminus of the enzyme.

The following methodologies are utilized to isolate these various epitope labeled rWS asparaginase proteins:

(1) GST-sepharose (Pharmacia AB, Upsala, Sweden) column chromatography is utilized to purify the GST-labeled rWS asparaginase enzyme expressed from the pGEX-2T-WSA vector, followed by cleavage by thrombin.

(2) Protein-G-sepharose immobilized anti-HA and anti-FLAG antibodies (Pharmacia AB, Upsala, Sweden) is utilized to affinity purify the HA- or FLAG-labeled rWS asparaginase enzyme.

(3) Nickel resin (Ni-NTA (nitilo-tri-acetic acid resin); Novagen, Inc., Chatsworth, Calif.) is used to affinity purify p-His-labeled rWS asparaginase enzyme.

More specifically, for example, production of poly-histidine (p-His)-labeled, glutathione-S-transferase (GST)-rWS asparaginase requires the induction of positively transformed *E. coli* with IPTG, followed by harvesting of the bacteria (see Hochuli, E., & Dobell, N, New metal chelate absorbents selective for protein and peptide containing neighboring histidine residues, 411 J. Chromatography 177 (1987)). In such expression systems, vectors such as pGEX-2T and pET-28a expression vectors may be utilized to facilitate the expression of a non-epitope-labeled form of the rWS asparaginase following IPTG induction. The p-His-labeled constructs, localized in the N-terminus of the rWS asparaginase, can then be sub-cloned into the BamH1 to EcoR1 site of the pET-28a vector (Novagen, Inc., Chatsworth, Calif.) for expression of the p-His-labeled rWS enzyme.

Example 7

Purification of *Wolinelia succinogenes* Asparaginase

The native, homotetrameric form of *W. succinogenes* asparaginase was purified according to the following methodology. *W. succinogenes* cell lysates were prepared by subjecting bacteria cultured and frozen in accordance with Example 1 to 3 to 4 freeze/thaw cycles with sonication, followed by high-speed centrifugation to remove cell debris. After centrifugation, the supernatant was brought to 0.1 M concentration of ammonium sulfate at a temperature of 4° C. The mixture was then brought to a final volume of 120% by the addition of a 2% protamine solution, followed by centrifugation for 30 min. at 21,000×g. The supernatants were recovered, pooled, and brought to a 50% ammonium sulfate saturation and equilibrated for 30 minutes on ice with continuous stirring. The resulting solution was then dialyzed against 0.01 M potassium phosphate buffer (pH 8.0) and applied to a 3 cm×20 cm hydroxyapatite column (prepared by: Pharmacia, Inc.) equilibrated with 0.1 M potassium phosphate buffer pH 8.0.

The *W. succinogenes* asparaginase was eluted from the hydroxyapatite column utilizing step-wise concentrations of phosphate buffer (i.e. 0.10, 0.20, 0.25, 0.30, 0.35 M phosphate buffer, pH 8.0). The eluted fractions (10 mL/fraction) were collected, assayed for asparaginase enzymatic activity, and pooled. The enzymatically-active fractions were dialyzed against 0.1 M sodium borate buffer (pH 7.0) and applied to a 3 cm×20 cm DEAE-Sephadex column (prepared by Pharmacia, Inc.) equilibrated in 0.1 M sodium borate buffer, pH 7.0. The enzyme was eluted by use of a linear gradient of sodium chloride (0 to 1.0 M) in 0.1 M sodium borate buffer (pH 7.0). 60 mL asparaginase-containing fractions were retained. *W. succinogenes* L-asparaginase prepared utilizing this methodology has been shown to be homogeneous by SDS-PAGE electrophoresis and silver staining.

*E. coli* EC-2 asparaginase (Merci, Sharp & Dohme, West Point, Pa.) was further purified by gel filtration on Ultragel® AcA-44 (LKB Instruments, Inc., Rockville, N. Mex.). *Erwinia carotovora* asparaginase (Microbiological Research Establishment, Salisbury, England) was provided by Pharmaceutical Resources Branch of the National Cancer Institute.

Example 8

Determination of the Biochemical Characteristics of Asparaginase

The X-ray crystallographic structures of several microbial asparaginases have been elucidated (see Lubkowski, J. & Palm, N. (1996), supra). Recombinant *W. succinogenes* asparaginase and 121 analogs which possesses acceptable clinical properties have the following characteristics: (1) catalytic activity in vitro, (2) preferably a native-protein-like homotetrameric structure required for functional enzymatic catalysis, and (3) with respect to the recombinant form of *W.*

*succinogenes* asparaginase, similar to that of the native, homotetrameric form of *W. succinogenes* asparaginase, greater substrate specificity for L-asparagine and not catalyzing the deamidation of L-glutamine to any physiologically significant degree.

In order to quantitate the biochemical characteristics of both the native, homotetrameric and recombinant asparaginase enzymes, $K_m$ and $V_{max}$ enzyme kinetics, substrate specificity, pH optimum, and temperature optimum can be determined. In addition, SDS-PAGE under both reducing and non-reducing conditions, followed by silver and Coomassie Blue staining of the gels, can be utilized to establish enzyme homogeneity, evaluate subunit composition, and determine enzyme molecular weight (see Park, R. & Liu, K., A role for Shc, grb2 and raf-1 in FcR1 signal relay, 271. J. Biol. Chem. 13342 (1996).

The enzymatic activity of L-asparaginase can be quantitatively determined by the amount of ammonia produced upon the hydrolysis of 0.08 M L-asparagine using 0.01 M sodium phosphate buffer (pH 7.0) as the reaction buffer (see Durden, D. L. & Distasio, J. A. (1980), supra). The assay mixture can consist of 10 to 40 IU of a homogeneous solution of L-asparaginase enzyme diluted to 2.0 ml with 0.01 M sodium phosphate buffer (pH 7.0). Briefly, this assay system measures the deamidation of L-asparagine indirectly by quantitating the release of $NH_3$ as colormetrically-detected by Nessler's Reagent. A standard curve of $NH_4OH$ may be prepared to initially derive an extinction coefficient for $NH_3$, based upon absorbance at 420 nm. The enzyme reaction may be initiated by the addition of the L-asparagine substrate (0.04 M). For the determination of $K_m$ and $V_{max}$ enzyme kinetics, a more sensitive NADPH-dependent L-asparaginase assay system can utilized (see Distasio, J. A. & Niederman, T. (1976), supra).

Example 9

Therapeutic Administration of Asparaginase in Murine Animal Models

The recombinant and native forms of *W. succinogenes* asparaginase and analogs thereof, including 121 analogs, may be titrated between 5 and 50 IU per injection and the mice can receive up to 3 daily intraperitoneal (I.P.) injections at each dose. Toxicological and pharmacological studies for the native and recombinant enzymes and analogs can be performed by the determination of serum enzyme activity (i.e. serum enzyme half-life) as described in Example 8.

Example 10

Determination of Asparaginase Enzymatic Activity (Serum Half-life)

Serum half-life determinations can be performed on Balb/c mice intraperitoneally-injected with 5 or 10 IU of native (WS) or recombinant (rWS) *Wolinelia succinogenes* asparaginase or 121 analogs. Enzyme half-life measurements can be performed by a slight modification of a previously published procedure (see Durden, D. L., et al., kinetic analysis of hepatotoxicity associated with anti-neoplastic asparaginases, 43 Cancer res. 1602 (1983)). Specifically, enzyme half-life measurements can be performed by obtaining a 5 µl blood sample from the tall vein of the Balb/c mice at specific intervals following the I.P. injection of the WS or rWS asparaginase. The blood samples are then kept on ice until all samples had been collected. Once sampling was completed, each 5 µl blood sample can then be immediately pipetted into 0.5 ml of cold 1.19% sodium chloride in 0.1 M sodium phosphate buffer (pH 7.0) and mixed by vigorous vortexing.

To determine serum asparaginase activity (and hence serum half-life), two 0.2 ml aliquots from each time point can be equilibrated in a 37° C. water bath. The enzymatic reaction is subsequently initiated by the addition of 0.03 ml of 0.04 M L-asparagine, pre-equilibrated to 37° C. prior to addition, into one of the 0.2 ml samples. The other 0.2 ml aliquot receives only 0.3 ml of distilled water and will serve as a control "blank." The substrate-containing reaction tube may be incubated at 37° C. for 1 hour after which the reaction is stopped by the addition of 0.2 ml of 5% TCA. In addition, a 0.2 ml aliquot of 5% TCA is also added to the control "blank." The tubes are then centrifuged at 5000×g to remove the resulting TCA-produced precipitate. Enzymatic activity may be colormetrically-determined by the addition of a 0.2 ml aliquot of the substrate-containing sample to 0.2 ml of distilled water and 0.2 ml a freshly-prepared Nessler's Reagent and the absorbance at 420 nm is read using a spectrophotometer (Gilford Instrument Laboratories, Oberlin, Ohio).

Example 11

Determination of the Anti-Neoplastic Activity of Asparaginase

The anti-neoplastic (anti-lymphoma) activity of homogeneous preparation of both native (WS) and recombinant (rWS) *W. succinogenes* asparaginase, as well as that of native *E. coli* (EC) and *E. carotovora* (Erw) asparaginases and 121 analogs, can be determined utilizing the 6C3HED Gardner lymphosarcoma cell line implanted in C3H mice. This lymphoid tumor originated in the thymus of C3H mice given high doses of estradiol and was perpetuated by serial transplantation in the C3H mice. In these studies, the tumor is maintained as an ascites tumor through I.P injection of $2 \times 10^8$ viable lymphosarcoma cells in 0.1 ml of PBS (pH 7.0).

To determine asparaginase anti-tumor activity, $2.5 \times 10^6$ viable 6C3HED lymphosarcoma cells from an ascites tumor is injected in a volume of 0.05 ml of PBS (pH 7.0) subcutaneously in the left ventral groin of 9 to 12 week-old C3H mice. Similarly, in another series of experiments, $2.5 \times 10^6$ viable P1798 lymphosarcoma cells from an ascites tumor is injected in a volume of 0.05 ml of PBS (pH 7.0) subcutaneously in the left ventral groin of 9 to 12 week-old Balb/c mice (see Jack, G. W., et al., The effect of histidine ammonia-lyase on some murine tumors, 7 Leukemia Res. 421 (1983)). Palpable solid tumor growth generally occurred within 4 to 7 days after injection of the lymphosarcoma cells. Changes in solid tumor volume are then subsequently measured by daily caliper-based measurement of tumor dimensions along three axes. When the average tumor volume reaches 1 cm³, intraperitoneal injection of asparaginase can be performed. A total dosage of 3 or 6 IU of asparaginase may be administered in a total of six I.P injections of 0.5 or 1.0 IU asparaginase/injection, respectively. Injections may be administered twice daily for three consecutive days.

The negative control animal group receives I.P. injections of 0.01 M phosphate buffer (pH 7.0) utilizing a similar injection schedule. *E. coli* and *E. carotovora* asparaginases serve as positive controls for comparison of anti-tumor activity in this series of experiments. Student's t-test will be utilized for all statistical analysis of data.

Example 12

Immune Cross-Reactivity *W. succinogenes* Asparaginase

This example describes how it was determined if antibodies in patients known to neutralize *E. coli* asparaginase react with *W. succinogenes*. Specifically, an ELISA assay was performed to make this determination, as described below.

The ELISA assay was performed on two 96 well microtiter plates, as follows: asparaginase (EC on one plate, WS on the other) was diluted in carbonate buffer (prepared by dissolving 1.59 g $Na_2CO_3$, 2.93 g $NaHCo_3$, and 0.2 g $NaN_3$ in 1 L of purified water; pH was adjusted to 9.0-9.5 using IN HCl or IN NaOH; the buffer was stored at 4° C. for no more than two weeks before use) to a final concentration of 0.10 IU/mL. 54 wells on each plate were coated with 100 µL of the respective diluted asparaginase solution and incubated overnight at 4° C. after being wrapped in aluminum foil to allow the enzyme to become associated with the plates.

The following morning the plates were removed and the solution from each of the wells was removed. These wells were then blocked with 300 µL of a 1 mg/mL solution of BSA-PBS blocking buffer, pH 7.0 (prepared fresh by adding the appropriate amount of bovine serum albumin to PBS buffer, 0.010 M sodium phosphate, pH 7.0-7.2, 0.9% saline). The plates were then incubated for 1 hour at room temperature. Thereafter, the plates were washed with 300 mL of saline-Tween buffer (0.145 M NaCl, 0.05% Tween 20) per well using a Dynatech Ultrawash plate washer.

The antibodies used to screen the two plates were diluted as follows: 1:100, 1:1,000; 1:2,000; 1:4,000; 1:8,000; 1:16,000; and 1:32,000. As a control, serum from a normal human patient was used. Patient serum and rabbit anti-EC asparaginase serum and normal human serum were diluted in PBS-Tween (PBS containing 0.05% Tween 20) and 100 µL of each dilution was placed on each plate in triplicate according to the following grid:

| CONTROL | | | HUMAN PATIENT | | | RABBIT ANTIBODIES | | |
|---|---|---|---|---|---|---|---|---|
| 1 | 2 | 3 | 1 | 2 | 3 | 1 | 2 | 3 |
| 1:1,000 | 1:1,000 | 1:1,000 | 1:1,000 | 1:1,000 | 1:1,000 | 1:1,000 | 1:1,000 | 1:1,000 |
| 1:2,000 | 1:2,000 | 1:2,000 | 1:2,000 | 1:2,000 | 1:2,000 | 1:2,000 | 1:2,000 | 1:2,000 |
| 1:3,000 | 1:3,000 | 1:3,000 | 1:3,000 | 1:3,000 | 1:3,000 | 1:3,000 | 1:3,000 | 1:3,000 |
| 1:4,000 | 1:4,000 | 1:4,000 | 1:4,000 | 1:4,000 | 1:4,000 | 1:4,000 | 1:4,000 | 1:4,000 |
| 1:8,000 | 1:8,000 | 1:8,000 | 1:8,000 | 1:8,000 | 1:8,000 | 1:8,000 | 1:8,000 | 1:8,000 |
| 1:16,000 | 1:16,000 | 1:16,000 | 1:16,000 | 1:16,000 | 1:16,000 | 1:16,000 | 1:16,000 | 1:16,000 |
| 1:32,000 | 1:32,000 | 1:32,000 | 1:32,000 | 1:32,000 | 1:32,000 | 1:32,000 | 1:32,000 | 1:32,000 |

After adding the above dilutions, the plates were incubated for at least 1.5 hour at room temperature, followed by washing each plate three times with saline-Tween as described above. A 1:1,000 dilution of Horse radish peroxidase-conjugated goat anti-human immunoglobulin (BioSource International) was then prepared in PBS-Tween. 100 µL of the HP-conjugated anti-human Ig was then added to each well. The plates were then covered and allowed to incubate at room temperature for 1 hour.

After the 1 hour incubating each plate was again washed three times with saline-Tween, as before. To detect antibody binding, 100 µL of OPD (o-phenylenediaminedihydrochloride) substrate (40 mg of OPD in 100 mL a citrate phosphate buffer (0.1M, pH 6.0, prepared by combining a solution containing 13.4 g $Na_2HPO_4$ $7H_2O$ (dibasic) in 500 mL distilled water with an amount of a solution containing 9.60 g citric acid (anhydrous) in 500 mL distilled water sufficient to adjust the pH to 6.0) with 334 µL of 3% $H_2O_2$ prepared immediately before use and kept at room temperature in the dark) was added to each well and allowed to incubate at room temperature in the dark for approximately 40 minutes. The reaction in each well was stopped by adding 100 µL of 1 M phosphoric acid. The absorbance of each well was then measured at 40 nm.

Figure 8:
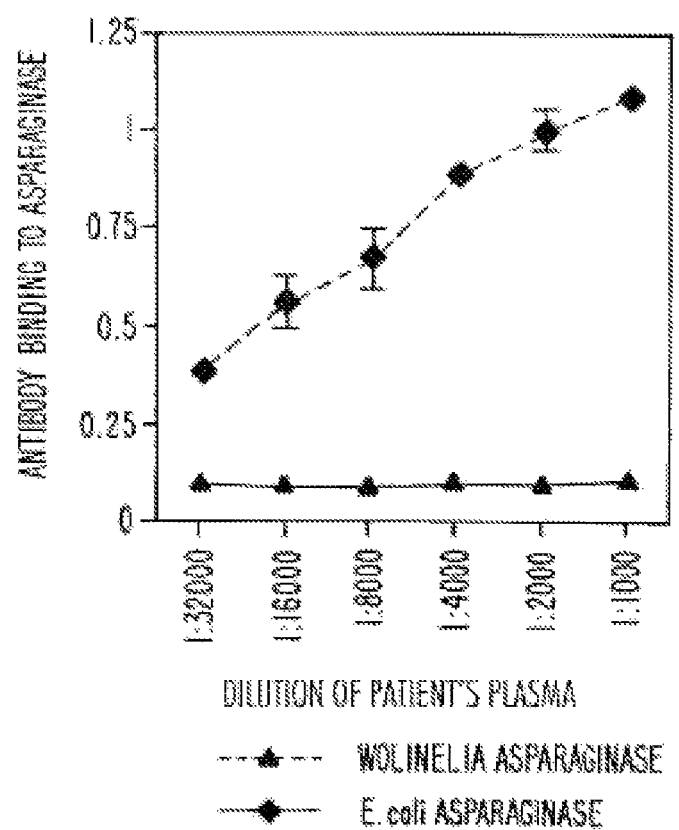
FIG. 8: Illustrates the lack of cross-reactivity between different dilutions of a patient's plasma known to contain high-titer neutralizing antibodies against *E. coli* asparaginase and the *W. succinogenes* enzyme.
Figure 9:
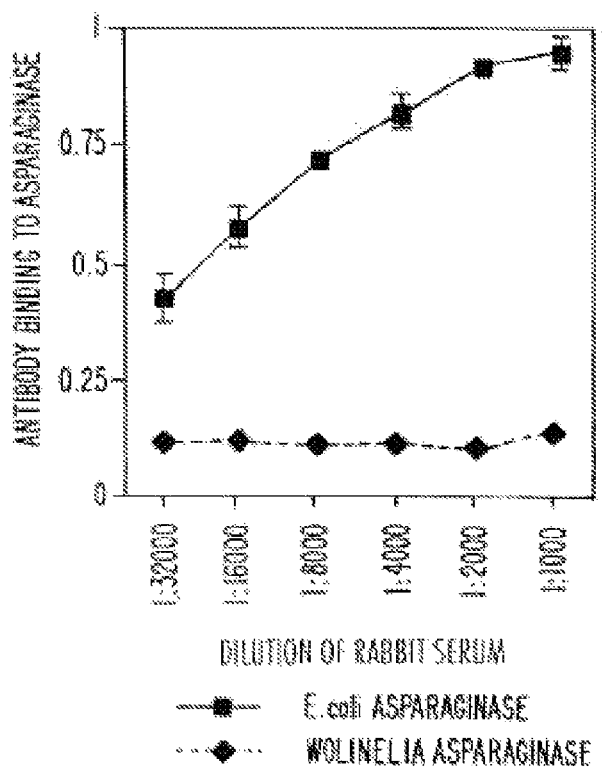
FIG. 9: Illustrates the lack of cross-reactivity between different dilutions of polyclonal high-titer neutralizing antibodies against *E. coli* asparaginase and asparaginase derived from *W. succinogenes*.

As is shown in FIG. 8, high titer neutralizing antibodies against the *E. coli* enzyme present in patient plasma failed to bind to the *Wolinella* asparaginase. This figure shows one of 6 plasma specimens collected from patients known to be allergic to the *E. coli* enzyme as well as rabbit antisera raised against the *E. coli* asparaginase. None of these anti-*E. coli* reactive antisera bind or neutralize the *Wolinella* asparaginase activity (FIGS. 8 and 9). From these data it was concluded that the *W. succinogenes* enzyme is immunologically distinct from *E. coli*, and that the *Wolinella* enzyme can be used in patients allergic to the *E. coli* enzyme (as exemplified by titration of patient plasma shown in FIG. 8 and rabbit anti-*E. coli* antisera shown in FIG. 9).

A highly specific antisera against the *W. succinogenes* enzyme which does not cross react with *E. coli* asparaginase in Western blot analysis has also been prepared. This reagent is useful for performing immunological characterizations of the native, recombinant, and various analogs disclosed herein. Analysis of native, recombinant, and analog forms of *W. succinogenes* asparaginase for this type of immunologic cross reactivity will be useful in characterization of genetically and chemically modified proteins. Importantly, these analyses will be applied to analysis of clinical specimens during phase I and II clinical trials of the different forms of the *W. succinogenes* enzyme, e.g. 121 analogs.

Example 13

Methodology for Protein Modification Using Acylation

Protein acylation is accomplished by using different acylating agents, such as acyl halides (e.g. acyl chlorides), carbodiimide compounds, or acid anhydrides, each with a different number of carbon atoms comprising a straight or branched aliphatic chain attached to the carbonyl, or the modified carbonyl (in the case of carbodiimides), carbon atom. The acylating agents contemplated for use in practicing this invention have the ability to react with a polar group contained within the peptide sequence of a protein to form an amide side chain. The polar group is the side chain of any of the amino acids in the primary sequence, for example, the amine group of lysine or arginine, the hydroxy group of threonine, serine, or tyrosine, or the thiol group of cysteine. Preferably, the reaction is carried out under conditions which do not substantially reduce (i.e. reduce by more than 90%, preferably less than 50%, and more preferably less than 25%) the catalytic activity of the enzyme.

Briefly, the chemical reaction was started at zero time with the dropwise addition of acetyl chloride to 5,000 IU of asparaginase, derived from either *E. coli* or *W. succinogenes*, in a volume of 10 mL of 0.1 M borate buffer at pH 8.5. The final concentration of each acid chloride is 0.1 M. The chemical reaction involves a nucleophilic attack of the polar group, e.g.

the free amino group, within the peptide sequence of the protein, e.g. asparaginase molecule, (which is maintained in an unprotonated form in the borate buffer, pH 8.5) with the reactive acylating agent. The polar group reacts with the acylating agent yielding an aliphatic hydrocarbon modified amino acid side chain. If the acylating agent is an acyl halide, an equivalent of the respective hydrohalic acid is produced. Thus, if the acylating agent is acyl chloride and the amino acid to be modified is lysine, then the reaction yields an acylated amino group and 1 equivalent of HCl (see FIG. 7). To prevent acid conditions from destroying the structure of the protein molecule (decreasing yield of enzyme, Table 1, below), a 1 N solution of NaOH is added drop-wise to the reaction mixture every 5-10 seconds. Aliquots of 2 mL were removed at the indicated reaction times (see Table 1, below), and immediately dialyzed against 0.01 M phosphate buffer at pH 7.0. Protein concentration is measured by Bradford method. Enzyme activity is determined by the amount of ammonia produced upon hydrolysis of L-asparagine (0.08 M L-asparagine) with a Nessler's reagent (see Durden, D. L. et al, Cancer Res, 40: 1125, (1980)). Free amino groups are measured by the method of Habeeb (see Habeeb, A. F. S. A., Analytical Biochemistry, 14:328, 1966). Table 1 is as follows:

Effect of acylation with acetyl chloride on *W. succinogenes* asparaginase

|  | Reaction time[a] (hr) | Specific activity[b,c] (IU/mg) | Reduction of free amines[d] (%) | Recovery of activity[c] (%) | Half-Life (hr) |
|---|---|---|---|---|---|
| Native enzyme | 0 | 150.0 | 0 | 100.0 | 1.8 |
| Derivatize d enzyme | 0.5 | 120.0 | 29.0 | 80.0 | 8.0 |
|  | 1.0 | 129.0 | 26.8 | 86.0 | 8.2 |
|  | 2.0 | 130.0 | 32.4 | 86.6 | 7.4 |
|  | 3.0 | 120.0 | 30.2 | 80.0 | 7.3 |
|  | 4.5 | 90.0 | 31.3 | 60.0 | 6.2 |

[a]The reaction is started at time 0 with the addition of acetyl chloride to 5,000 IU of *W. succinogenes* asparaginase in 10 ml of 0.1M borate buffer, pH 8.5. Aliquots of 2.0 ml are removed at the times indicated and dialized against 0.01M phosphate buffer, pH 7.0.
[b]Protein is measured in triplicate by method of Bradford.
[c]Enzyme activity is measured by determining the amount of ammonia produced upon hydrolysis of L-asparagine with Nessler's reagent.
[d]Free amino groups are measured by method of Habeeb.

Acyl modification is performed with acylating agents of different aliphatic chain lengths, e.g. a 2 carbon aliphatic chain (C2), a 4 carbon aliphatic chain (C4), a 6 carbon aliphatic chain (C6), etc. Importantly, each specific protein (e.g. asparaginase) has different numbers of free polar groups in different positions within the protein molecule and hence each protein is optimally modified with a different length acylating agent which conjugates a different aliphatic carbon chain to the free amino groups. These include, for example, acetyl chloride (C2), butyryl chloride (C4), hexanoyl chloride (C6), decanoyl chloride (C10), as well as the use of branched chain acid chlorides including trimethylacetyl chloride. Also, different acylating agents may be used for different proteins. For example, with some proteins acetyl chloride may be used, whereas for other proteins acetic anhydride may be the best acylating agents. By way of illustration, the covalent modification of the *W. succinogenes* asparaginase with the acetyl chloride is presented in Table 1.

A. Results of Modification

There are a number of problems that have been associated with the use of enzymes for therapeutic purposes. Many of these enzymes have extremely short half-lives which severely limits their effectiveness in vivo. The modification of proteins using organic modification techniques of the present invention is a promising solution to many of these problems. The C2 modification of *W. succinogenes* asparaginase results in an enzyme which has a half-life of 8.2 hours in mice as compared to the 1.8 hour half-life of the native enzyme. The increase in half-life is consistent with the time course of acetylation reaction (resulting in 20-40% decrease in enzyme activity while the activity of the *W. succinogenes* asparaginase decreases with the increasing reaction time). An about 80% recovery of enzyme activity after a 30 min. reaction time was observed, a time of maximum alteration of pharmacokinetic extension of half-life to 8.0 hours. Other modification procedures which involve polymerization (e.g. polyethylene-glycol modification) result in heterogenous groups of modified reaction products which may not be suitable for administration in humans. The acid chloride modification procedure is a systematic approach which does not yield such heterogeneity in reaction products (see FIG. 7). The greater reproducibility and more restricted nature of reaction products result in a well controlled modification of proteins and a more reliable product with predictable extension of half-life which decrease the immunogenicity, and with the advantage of being able to very carefully control the extent of modification of the polar groups present in a specific protein molecule. Current data modifying *W. succinogenes* asparaginase demonstrate that the enzyme is modified with a C2 acylation reaction which results in the augmentation of half-life approximately four fold. The modification of the free amino groups and the asparaginase molecule is responsible for extension of half-life. It is suggested that the extension of half-life will correlate with a decrease in the electrostatic charge, increase in hydrophobicity and decreased immunogenicity of the enzyme. The extension of half-life and decreased immunogenicity will increase the efficacy of the *W. succinogenes* enzyme when this drug is used in the treatment of acute lymphoblastic leukemia, autoimmune disease, or AIDS, for example, in humans. Through this modification procedure, we are able to generate foreign proteins which have lower immunogenicity, extended half-life, and augmented efficacy. With this systematic approach of modification, any protein can be modified and the modified protein can then be used in the treatment of human disease. Essentially, any protein that has polar groups available in its native state (essentially all known proteins) is amenable to the modification technique of the present invention. Hence this invention extends to all proteins currently used in treatment of human, animal and plant diseases.

121 Analogs

The methods and experiments described above, as well as those known in the art, may be applied to the 121 analogs of the present invention in addition to the following:

Lyophilized, purified *W. succinogenes* asparaginase provided by Dr. Donald Durden, UCSD School of Medicine (Part #50161; Lot #L0408004; Date Apr. 25, 2004) was used as a standard (for comparison with the 121 analogs of the present invention). The lyophilized asparaginase was dissolved in PBS (phosphate buffered saline) and stored at −80° C. The concentration of the asparaginase was calculated according to the instruction on the label of the vial (dissolve content of vial in 1.1 mL sterile 0.9% NaCl→get 8600 U/mL). The concentration in mg/mL was calculated for a specific activity of 230 U/mg.

Expression in Deep Well Plates

Expression experiments in deep well plates were done with Greiner BioOne 96 deep well plates containing 0.8 ml semi-synthetic medium and supplemented with 100 µg/ml Ampicillin. The main cultures were inoculated with 8 µl overnight cultures (grown in VYB supplemented with 100 µg/ml Ampicillin). Subsequently, the cultures were incubated at 30° C. for 24 hours.

Expression in Shake Flask

Shake flask expression experiments were done in 100 ml shake flask with 20 ml semi-synthetic medium and supplemented with 100 µg/ml Ampicillin. The main cultures were inoculated with overnight cultures (grown in VYB medium supplemented with 100 µg/ml Ampicillin) to an initial OD600 of 0.1. Subsequently, the cultures were incubated at 30° C. for 24 hours.

Sample Treatment

Samples (200 to 1000 µl) were taken after 24 hours if not mentioned elsewhere, centrifuged (deep well cultures: 3800 rpm, 15 min, 4° C.; shake flask cultures: 16000×g, 5 min, 4° C.) and the supernatant (cell free medium) was removed and stored for later analysis. Cells were broken according to the BugBuster treatment protocol from Novagen if not otherwise indicated. Briefly, the cell pellets were resuspended in Bug-Buster reagent and equalized to an optical density of 10. The cell suspension was incubated at 37° C. for 1 hour in Bug-Buster reagent supplemented with Lysonase. Insoluble cell debris was removed by centrifugation (deep well cultures: 3800 rpm, 30 min, 4° C.; shake flask cultures: 17000×g, 15 min) and supernatant (soluble fraction) was isolated. The pellet (insoluble fraction) was resuspended 2% SDS to the same volume as lysis buffer was added previously, followed by incubation for 40-60 min at 56° C. The samples were either directly applied for analysis or stored at −20° C. for later analysis. For some samples cell disruption by a French Press was used. Cell pellets were resuspended in disruption buffer (50 mM MES, 1 mM EDTA, pH 6.0 adjusted with NaOH) supplemented with Lysonase and disrupted by 2-3 passages in a French Press. Insoluble cell debris was removed by centrifugation at 4° C. and supernatant (soluble fraction) was isolated. All steps were performed on ice or at 4° C. The samples were either directly applied for analysis or stored at −80° C. (samples of 1 L cultures) or −20° C. (other samples) for later analysis.

Detection by SDS-PAGE

Precasted TGX "anykD" SDS Criterion gels from Bio-Rad were used with TGS buffer from Bio-Rad. 7.5 µl samples (cell fraction of cells equalized to OD600 of 10 or cell free medium) with 2.5 µl 4×LDS loading dye (reducing conditions) and, as a molecular weight standard, Mark 12 from Invitrogen were loaded. The separated proteins were visualized by staining with GelCode Blue Stain Reagent from Pierce.

Detection by Western Blot

SDS-PAGE was performed as described above. Samples (1.8 µl cell fraction of cells equalized to OD600 of 10 or cell free medium+1.8 µl PBS+2.5 µl 4×LDS loading dye, reducing conditions) were loaded. Blotting was performed for 10 min at 2.5 A using the Trans-Blot® Turbo™ Blotting System, Bio-Rad, with a nitrocellulose 0.2 µm membrane. The membranes were blocked with 5% skim milk in Tris buffered saline. Anti-Wolinase antibody (obtained from Dr. Donald Durden, UCSD School of Medicine) was used as primary antibody (1:30000 dilutions). Mouse anti-rabbit IgG Peroxidase conjugated (Pierce, SA1-9510) was used as secondary antibody (1:1000 dilutions). The detection was done using the Lumi-LightPLUS Horse radish Peroxidase Detection System (Roche Applied Science, #12015200001) according to the manufacturer's instructions.

Enzymatic Assay Using Nessler's Reagent

The asparaginase activity of the polypeptides according to the present invention may be determined by measuring the release of ammonia using Nessler's reagent. See e.g. Distasio, et al. (1976) J. Biol. Chem. 251: 6929-6933; and Broome (1965) J. Natl. Cancer Inst. 35:967-974, which are herein incorporated by reference in their entirety. In brief, the asparaginase containing sample and L-asparagine (substrate) are mixed at 37° C. and the reaction is stopped when cold TCA is added. The reaction mixture of enzyme, substrate and TCA is then added to a plate containing Nessler's reagent (mercuric iodide mixture, Merck KGaA, Darmstadt, Germany, #109028). After the plate is developed the absorbance at 405 nm is measured. Ammonium sulfate is used as the source of ammonia for the standard curve. Each series of plates handled in parallel include a standard series (ammonium sulfate). Samples (soluble fractions equalized to an optical density of 10) were diluted with BSA solution (1 mg/ml bovine serum albumin in 10 mM sodium phosphate pH 7.0) (typically 1:200 dilutions) and measured in duplicate. The ammonia concentration at four time points (10 min, 20 min, 30 min and 45 min) was determined. Linear regression was used to determine the enzyme activity, measured in micromoles of ammonia per minute per ml. The specific asparaginase activities using a similar procedure for *W. succinogenes* asparaginase was found to be between 177 U/mg and 270 U/mg. Thus, for the 121 analogs, a value of 270 U/mg was used to calculate the protein concentration in g/L.

Dual Assay

Asparaginase enzyme activity and glutaminase enzyme activity of the 121 analogs may be readily determined using methods disclosed herein as well as those known in the art. For example, a qualitative assay of L-asparaginase and L-glutaminase may be carried out using a rapid assay method ((Gulati et al. (1997) Lett. Appl. Microbiol. 24:23-26) by, for example, adding 0.2 ml of sample to 10 ml of water containing asparagine and glutamine respectively and 0.001% of phenol red dye. Break down of L-asparagine and glutamine renders the solution basic due to release of ammonia, changing the color of the solution from yellow to red. See also Rizzari et al. (2006) Haematologica 91(1):24-31. A quantitative assay for L-asparaginase and L-glutaminase activities (Shirfrin et al. (1974) J. Biol. Chem. 249:133-1340) may be carried out by using, for example, 189 mM L-asparagine or 189 mM L-glutamine as substrate in 50 mM Tris buffer (pH 8.6) and reading the absorbance at 436 nm. Cell-free broth was used as the source of crude enzyme. Ammonium sulfate solution was used for preparation of a standard curve. One International Unit (IU) of asparaginase activity is defined as the amount of enzyme required to release 1 µmol of ammonia per ml per min at pH 8.6 at 37° C. Glutaminase activity may also be determined by continuous coupled spectrophotometry based on L-glutamine hydrolysis and L-glutamate oxidation, with L-glutamate dehydrogenase as an auxiliary enzyme and beta-nicotinamide adenine dinucleotide as a redox agent. However, the following dual assay was used to measure kinetic rates of substrate utilization of the 131 analogs of the present invention.

All reagents were diluted to their final concentration in phosphate buffer. The reagents used were as follows:

| | |
|---|---|
| 5 mM | NADH (freshly made before assay) |
| 20 IU/ml | L-Glutamic Dehydrogenase |
| 0.1M | α-Ketoglutarate |
| 0.1M | Substrate (L-Asparagine or L-Glutamine) |
| Enzyme | (20 IU/ml Elspar or 121 analog, 215 IU/ml Wolinase) |
| Phosphate Buffer | 0.01M pH 7.0 + 1 mg/ml BSA |
| Quartz Cuvette | (1 cm path length) |

This dual assay protocol assumes a $1.0 \times 10^{-3}$ M Substrate concentration and NCI-Wol as the enzyme; however, the actual substrate concentration will vary for each enzyme and depending on the desired substrate conditions. Therefore, the stock substrate concentration can be adjusted accordingly to make pipetting feasible. BSA (bovine serum albumin) was included in the phosphate buffer to prevent L-glutamic dehydrogenase and the enzymes from sticking to the containing vials and cuvettes. More robust results and better repeatability were obtained by the inclusion of BSA. Therefore, the phosphate buffer preferably includes 1 mg/ml BSA. This assay is very sensitive to free NH4 and so even very low contaminating levels of ammonia can provide false positives. Consequently, all reagents must be checked with Nessler's reagent to test for background NH4 and dialyzed accordingly before use in the assay.

Prior to starting the assay the spectrophotometer was programmed for kinetic readings and absorbance readings at 340 nm every 20 seconds for 30 minutes. 940 µl of a mixture comprising 50 µl L-glutamic dehydrogenase (1 IU), 50 µl α-ketoglutarate (5 µMol), 2.15 IU enzyme, and phosphate buffer were added to a cuvette. The spectrophotometer was referenced at 340 nm with the cuvette containing the mixture. Due to the lack of NADH in the mixture at this point an absorbance close to zero should be observed. Then 50 µl NADH (250 nMol) was added to the cuvette and mixed and immediately after, kinetic readings were taken. A flat and constant absorbance somewhere around 1 should be observed. The absorbance for the first five minutes was observed for any contaminating ammonia, i.e. observed for a decline in the initial absorbance. Immediately after the first five minutes, provided that the absorbance measurements were still consistently close to 1, 10 µl of substrate was added into the cuvette and mixed so as to not disrupt the curve. This step does not need to be accomplished exactly at the 5 minute mark, so long as the time when the substrate was introduced is taken into account. The reaction was allowed to proceed for the remaining 25 minutes and the data was collected for analysis.

121 Analog Results

Cytoplasmic 121 analogs having SEQ ID NO: 1 or SEQ ID NO:2 obtained from various strains and expression vectors exhibited up to about 40 U/ml asparaginase activity at $OD_{600}$=10. An activity of 40 U/ml corresponds to a titre of about 170 mg/L, assuming a specific activity of 230 U/mg. Only small amounts of the analog were following in the insoluble fractions and in the cell free medium.

Periplasmic 121 analogs having SEQ ID NO:3 obtained from various strains and expression vectors exhibited up to about 60 U/ml asparaginase activity at $OD_{600}$=10 which is about 50% higher than the most active cytoplasmic 121 analogs. Only small amounts of the analog were following in the insoluble fractions and in the cell free medium.

Periplasmic 121 analogs having SEQ ID NO:4 obtained from various strains and expression vectors exhibited about 110-130 U/ml asparaginase activity at $OD_{600}$=10 which is greater than about 50% more than the most active cytoplasmic 121 analogs. An activity of 130 U/ml corresponds to a titre of about 565 mg/L, assuming a specific activity of 230 U/mg. Only small amounts of the analog were following in the insoluble fractions and in the cell free medium.

Expression of periplasmic 121 analogs were found to have a lower negative effect on the growth of the host strains as compared to the expression of cytoplasmic 121 analogs. There was little to no observable effect on asparaginase activity resulting from storage at 4° C. or −20° C. or resulting from the cell disruption method (BugBuster v. French Press).

The following Table 2 summarizes some of the results of the dual assay.

TABLE 2

| | Max Rate (abs/sec) Asparagine | Max Rate (abs/sec) Glutamine | Fold Δ Utilization (rate asp/rate glut) | Approx IU/ml | Approx Total IU |
|---|---|---|---|---|---|
| pCKL 1028 (SEQ ID NO: 3, periplasmic expression using MalE signal sequence and rhaB promoter) | −0.001729 | −0.000052 | 33.3 | 639 | 28,736 |
| pCKL 1029 (SEQ ID NO: 4, periplasmic expression using SRP signal sequence and rhaB promoter) | −0.001865 | −0.000126 | 14.8 | 668 | 16,695 |
| pCKL 1030 (SEQ ID NO: 1, cytoplasmic expression using a rhaB promoter) | −0.002729 | −0.000358 | 7.6 | 161 | 4,017 |
| pCKL 1031 (SEQ ID NO: 1, cytoplasmic expression using a rhaB promoter) | −0.002133 | −0.000205 | 10.4 | 37 | 930 |
| pCKL 4008 (SEQ ID NO: 4, periplasmic expression using SRP signal sequence and melA promoter) | −0.001741 | −0.00008 | 21.8 | 5,884 | 205,954 |
| NCI-WOL P121 | −0.003905 | −0.001333 | 2.9 | n/a | n/a |

As shown, the 121 analogs of the present invention exhibit higher rates of asparaginase activity over their rates of glutaminase activity (Fold Δ Utilization) as compared to P121 and of the 131 analogs, periplasmic 121 analogs exhibit higher values for Fold Δ Utilization that that of the cytoplasmic 121 analogs. Of the 121 analogs, clone pCKL 4008, which is a periplasmic (SRP signal sequence) 121 analog having SEQ ID NO:4, exhibited the best kinetic rates in view of the approximate total IU.

Figure 10A:
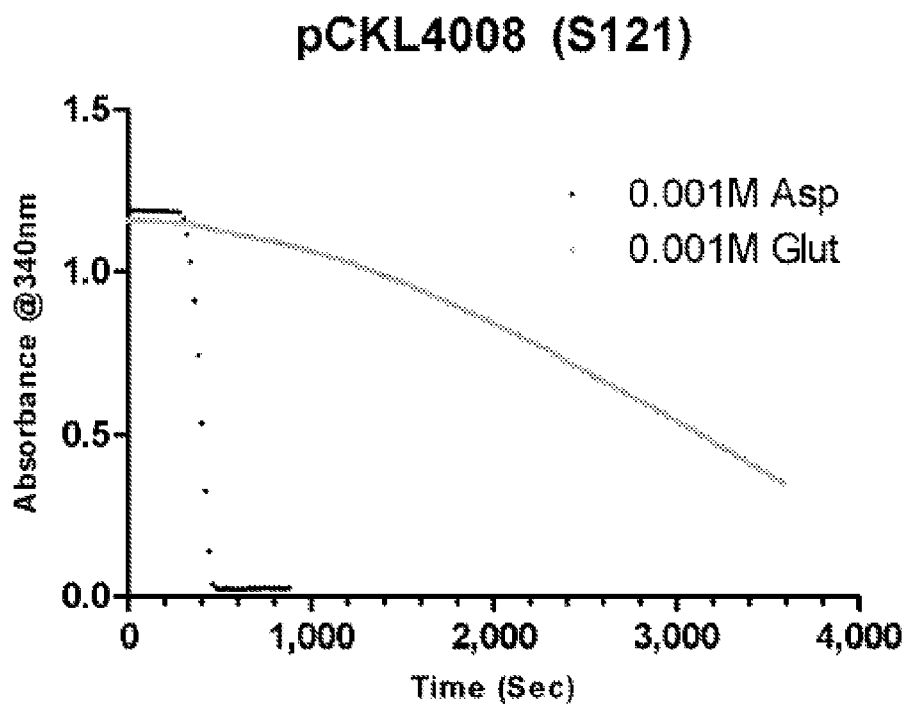
FIGS. 10A-10C: Are graphs showing the kinetic enzymatic activities of a 121 analog (FIG. 10A), Elspa® (FIG. 10B) and P121 (FIG. 10C).
Figure 10B:
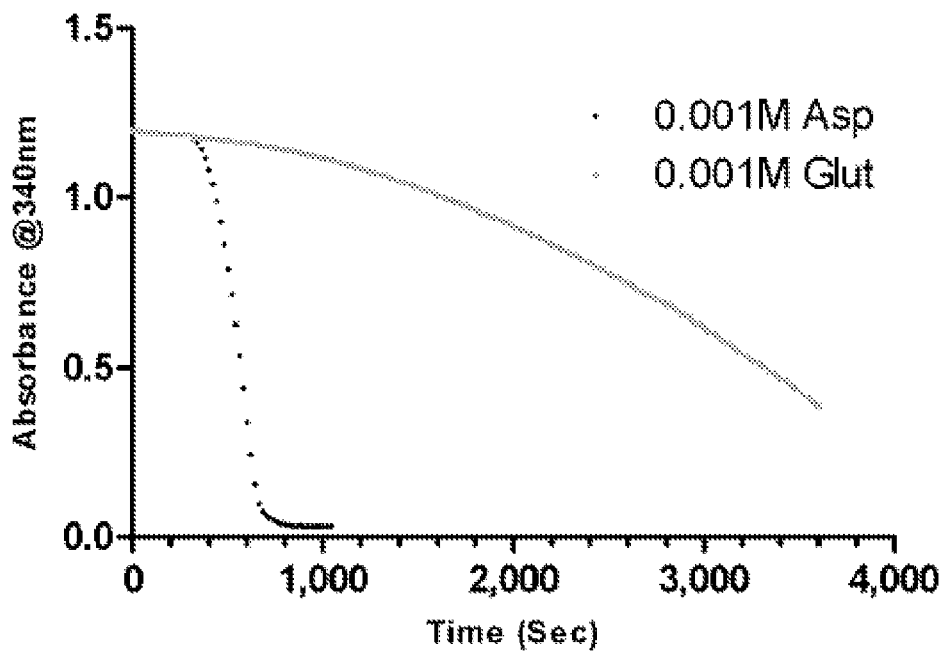
Figure 10C:
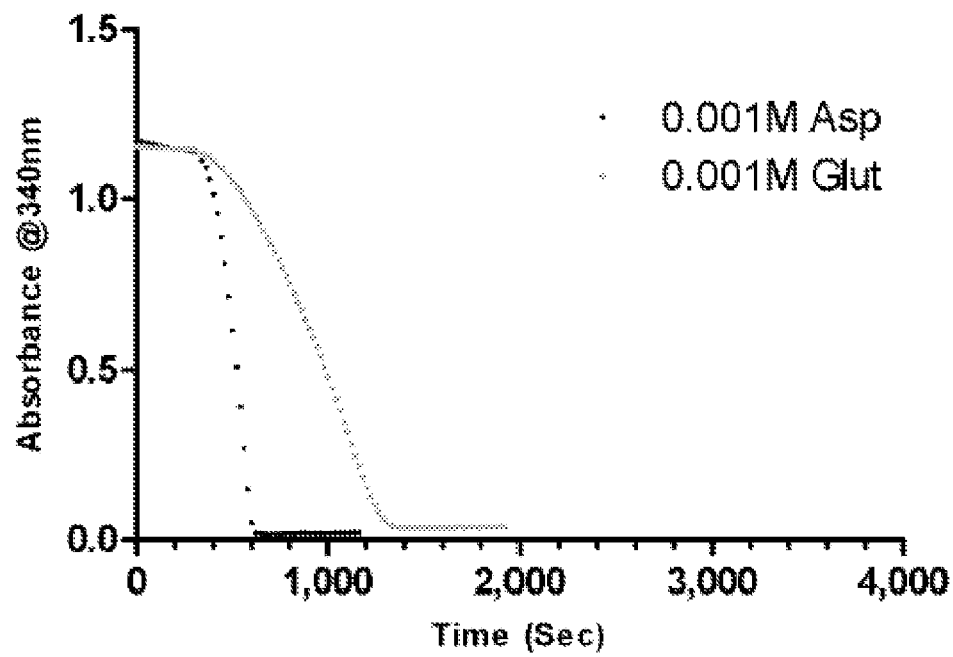

As compared to Elspar® (an E. coli asparaginase), pCKL 4008 has a faster kinetic rate of asparaginase activity and a similar kinetic rate of glutaminase activity, thus a higher Fold Δ Utilization. See FIGS. 10A and 10B. P121 has a kinetic rate of asparaginase activity similar to Elspar®, but an undesirable kinetic rate of glutaminase activity. See FIG. 10C.

Thus, in some embodiments, the present invention provides 121 analogs that exhibit kinetic rates of asparaginase activity that are greater than about 7.5 times that of their kinetic rates of glutaminase activity. In some embodiments, 121 analogs that exhibit kinetic rates of asparaginase activity that are about 7.6 to about 21.8 times that of their kinetic rates of glutaminase activity. In some embodiments, the 121 analogs exhibits kinetic rates of asparaginase activity that is between 7.5 to 22 times that of their kinetic rates of glutaminase activity.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein. The invention, therefore, is not to be restricted in any manner except in the spirit of the appended claims.

All references cited herein are hereby incorporated in their entirety. When used above, the term "including" means "including, without limitation," and terms used in the singular shall include the plural, and vice versa, unless the context dictates otherwise.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

I claim:

1. A recombinantly produced polypeptide comprising an amino acid sequence that corresponds to the protein having SEQ ID NO: 10 and has an amino acid residue other than proline at amino acid position 121, wherein said polypeptide has asparaginase activity and no glutaminase activity or reduced glutaminase activity, and wherein said polypeptide is a periplasmic protein.

2. A recombinantly produced polypeptide having an amino acid sequence that has at least 90-100%, 91-100%, 92-100%, 93-100%, 94-100%, 95-100%, 96-100%, 97-100%, 98-100%, 99-100%, or 100% sequence identity to SEQ ID NO: 1, SEQ ID NO: 2, SEQ ID NO: 3, or SEQ ID NO: 4, wherein said polypeptide has asparaginase activity and no glutaminase activity or reduced glutaminase activity, and wherein said polypeptide is a periplasmic protein.

3. The recombinantly produced polypeptide of claim 1, and further comprising a signal sequence having SEQ ID NO: 5 or SEQ ID NO: 6.

4. The recombinantly produced polypeptide of claim 1, wherein the amino acid residue is serine, alanine, glycine, cysteine, or threonine.

5. The recombinantly produced polypeptide of claim 1, wherein the polypeptide exhibits a kinetic rate of asparaginase activity that is greater than about 7.5 times that of its kinetic rate of glutaminase activity.

6. An isolated nucleic acid molecule which encodes the polypeptide of claim 1.

7. A host cell which contains the isolated nucleic acid molecule of claim 6.

8. A pharmaceutical composition comprising as an active pharmaceutical ingredient, the polypeptide according to claim 1, and a pharmaceutically acceptable carrier.

9. The pharmaceutical composition according to claim 8, wherein the polypeptide is provided in a therapeutically effective amount for treating a disease which responds to asparagine depletion and/or asparaginase therapy.

10. A method of treating a patient having a disease which comprises
    administering to the patient a therapeutically effective amount of a recombinantly produced polypeptide according to claim 1 to thereby result in an observable improvement in the clinical symptoms of the disease.

11. A kit which comprises at least one polypeptide according to claim 1 packaged together with a drug delivery device.

12. The recombinantly produced polypeptide of claim 1, wherein an SRP signal sequence was used to express the polypeptide.

13. The recombinantly produced polypeptide of claim 1, wherein a MalE signal sequence was used to express the polypeptide.

14. The recombinantly produced polypeptide of claim 1, wherein a melA promoter was used to express the polypeptide.

15. The recombinantly produced polypeptide of claim 1, wherein a rhaB promoter was used to express the polypeptide.

16. The recombinantly produced polypeptide of claim 1, wherein an SRP signal sequence and a melA promoter was used to express the polypeptide.

17. The recombinantly produced polypeptide of claim 1, wherein the polypeptide exhibits a kinetic rate of asparaginase activity that is 7.6 to about 21.8 times that of its kinetic rate of glutaminase activity.

* * * * *